(12) United States Patent
Roberts et al.

(10) Patent No.: US 12,727,883 B2
(45) **Date of Patent: *Sep. 8, 2026**

(54) SURGICAL STAPLING INSTRUMENT HAVING A TWO-POSITION LOCKOUT MECHANISM

(71) Applicant: Applied Medical Resources Corporation, Rancho Santa Margarita, CA (US)

(72) Inventors: Thomas M.B. Roberts, Rancho Santa Margarita, CA (US); Timothy M. Hopkins, Rancho Santa Margarita, CA (US); Quinton A. Quintana, Chino Hills, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/990,196

(22) Filed: Dec. 20, 2024

(65) Prior Publication Data

US 2025/0127508 A1 Apr. 24, 2025

Related U.S. Application Data

(63) Continuation of application No. 18/364,968, filed on Aug. 3, 2023, now Pat. No. 12,213,667, which is a (Continued)

(51) Int. Cl.

*A61B 17/068* (2006.01)
*A61B 17/072* (2006.01)

(52) U.S. Cl.

CPC .... *A61B 17/0686* (2013.01); *A61B 17/07207* (2013.01); *A61B 2017/07257* (2013.01);

(Continued)

(58) Field of Classification Search

CPC . A61B 17/068; A61B 17/0686; A61B 17/072; A61B 2017/07257;

(Continued)

(56) References Cited

U.S. PATENT DOCUMENTS

| | | | |
|---|---|---|---|
| 2,073,960 | A | 3/1937 | Crosby |
| 2,140,593 | A | 12/1938 | Pankonin |

(Continued)

FOREIGN PATENT DOCUMENTS

| | | |
|---|---|---|
| EP | 0 251 444 A1 | 1/1988 |
| EP | 0 492 283 A1 | 7/1992 |

(Continued)

OTHER PUBLICATIONS

European Patent Office, European Search Report for European Application No. 07784007.2, entitled "Surgical Stapler," dated Jun. 15, 2012, 6 pgs.

(Continued)

*Primary Examiner* — Linda J. Hodge
(74) *Attorney, Agent, or Firm* — John F. Heal

(57) ABSTRACT

Surgical stapler systems can include lockout mechanisms to restrict further movement of a jaw assembly and provide different functionality when a jaw assembly is empty and when a partially or fully fired reload cartridge is present in the jaw assembly. When the jaw assembly is empty, the empty jaw assembly lockout mechanism can arrest an open-close stroke of the jaw assembly. When an at least partially fired reload is present in the jaw assembly, a fired reload lockout mechanism can allow operation of the jaw assembly through a substantial portion of an open-close stroke, but restrict actuation of the jaw assembly in a firing stroke. The separate lockout mechanisms can be embodied in a single lockout lever actuatable by lockout actuators to three distinct positions or by two independently-operable lockout levers.

20 Claims, 17 Drawing Sheets

Related U.S. Application Data continuation of application No. 17/700,789, filed on Mar. 22, 2022, now Pat. No. 11,751,871, which is a continuation of application No. 16/801,788, filed on Feb. 26, 2020, now Pat. No. 11,311,293.

(60) Provisional application No. 62/811,457, filed on Feb. 27, 2019.

(52) U.S. Cl.
CPC ............... *A61B 2017/07271* (2013.01); *A61B 2017/07278* (2013.01); *A61B 2017/07285* (2013.01)

(58) Field of Classification Search
CPC ........... A61B 2017/07271; A61B 2017/07278; A61B 2017/07285; A61B 2017/00398; A61B 2017/0046; A61B 2090/0807; A61B 2090/0814; A61B 17/07207
USPC ..................... 227/175.2, 175.3, 175.4, 180.1
See application file for complete search history.

(56) References Cited

U.S. PATENT DOCUMENTS 2,351,608 A 6/1944 Greenwood
2,487,565 A 11/1949 Leber et al.
2,641,154 A 6/1953 Heller
3,076,373 A 2/1963 Matthews
3,077,812 A 2/1963 Dietrich
3,080,564 A 3/1963 Strekopitov et al.
3,203,220 A 8/1965 Kaepernik
3,252,643 A 5/1966 Strekopitov et al.
3,273,562 A 9/1966 Brown
3,373,646 A 3/1968 Ehlert
3,459,187 A 8/1969 Pallotta
3,494,533 A 2/1970 Green et al.
3,662,939 A 5/1972 Bryan
3,675,688 A 7/1972 Bryan et al.
3,692,224 A 9/1972 Astafiev et al.
4,261,244 A 4/1981 Becht et al.
4,281,785 A 8/1981 Brooks
4,304,236 A 12/1981 Conta et al.
4,312,363 A 1/1982 Rothfuss et al.
4,317,451 A 3/1982 Cerwin et al.
4,407,286 A 10/1983 Noiles et al.
4,434,796 A 3/1984 Karapetian et al.
4,442,964 A 4/1984 Becht
4,454,875 A 6/1984 Pratt et al.
4,522,327 A 6/1985 Korthoff et al.
4,527,724 A 7/1985 Chow et al.
4,589,582 A 5/1986 Bilotti
4,591,085 A 5/1986 Di Giovanni
4,606,344 A 8/1986 Di Giovanni
4,608,981 A 9/1986 Rothfuss et al.
4,610,383 A 9/1986 Rothfuss et al.
4,728,020 A 3/1988 Green et al.
4,805,823 A 2/1989 Rothfuss
4,892,244 A 1/1990 Fox et al.
4,923,350 A 5/1990 Hinksman et al.
4,941,623 A 7/1990 Pruitt
4,955,959 A 9/1990 Tompkins et al.
4,978,049 A 12/1990 Green
5,031,814 A 7/1991 Tompkins et al.
5,065,929 A 11/1991 Schulze et al.
5,071,052 A 12/1991 Rodak et al.
5,106,008 A 4/1992 Tompkins et al.
5,116,349 A 5/1992 Aranyi
5,129,570 A 7/1992 Schulze et al.
5,180,092 A 1/1993 Crainich
5,201,746 A 4/1993 Shichman
5,221,036 A 6/1993 Takase
5,236,440 A 8/1993 Hlavacek
5,240,163 A 8/1993 Stein et al.
RE34,519 E 1/1994 Fox et al.
5,275,323 A 1/1994 Schulze et al.
5,289,963 A 3/1994 McGarry et al.
D347,474 S 5/1994 Olson
5,307,976 A 5/1994 Olson et al.
5,308,576 A 5/1994 Green et al.
5,326,013 A 7/1994 Green et al.
5,350,400 A 9/1994 Esposito et al.
5,360,305 A 11/1994 Kerrigan
5,364,002 A 11/1994 Green et al.
5,366,479 A 11/1994 McGarry et al.
5,381,943 A 1/1995 Allen et al.
5,389,098 A 2/1995 Tsuruta et al.
5,395,034 A 3/1995 Allen et al.
5,397,046 A 3/1995 Savage et al.
5,413,267 A 5/1995 Solyntjes et al.
5,415,334 A 5/1995 Williamson, IV et al.
5,415,335 A 5/1995 Knodell, Jr.
5,439,155 A 8/1995 Viola
5,439,479 A 8/1995 Shichman et al.
5,445,304 A 8/1995 Plyley et al.
5,447,265 A 9/1995 Vidal et al.
5,452,836 A 9/1995 Huitema et al.
5,456,401 A 10/1995 Green et al.
5,458,279 A 10/1995 Plyley
5,462,215 A 10/1995 Viola et al.
5,464,144 A 11/1995 Guy et al.
5,465,895 A 11/1995 Knodel et al.
5,470,006 A 11/1995 Rodak
5,470,007 A 11/1995 Plyley et al.
5,470,008 A 11/1995 Rodak
5,470,009 A 11/1995 Rodak
5,472,132 A 12/1995 Savage et al.
5,480,089 A 1/1996 Blewett
5,485,952 A 1/1996 Fontayne
5,487,500 A 1/1996 Knodel et al.
5,489,058 A 2/1996 Plyley
5,497,933 A 3/1996 DeFonzo et al.
5,507,426 A 4/1996 Young et al.
5,507,773 A 4/1996 Huitema et al.
5,509,596 A 4/1996 Green et al.
5,509,920 A 4/1996 Phillips et al.
5,529,235 A 6/1996 Boiarski et al.
5,547,117 A 8/1996 Hamblin et al.
5,553,765 A 9/1996 Knodel et al.
5,554,164 A 9/1996 Wilson et al.
5,558,266 A 9/1996 Green et al.
5,562,241 A 10/1996 Knodel et al.
5,562,700 A 10/1996 Huitema et al.
5,562,701 A 10/1996 Huitema et al.
5,562,702 A 10/1996 Huitema et al.
5,564,615 A 10/1996 Bishop et al.
5,571,115 A 11/1996 Nicholas
5,571,285 A 11/1996 Chow et al.
5,579,978 A 12/1996 Green et al.
5,580,067 A 12/1996 Hamblin et al.
5,584,425 A 12/1996 Savage et al.
5,586,711 A 12/1996 Plyley et al.
5,588,581 A 12/1996 Conlon et al.
5,597,107 A 1/1997 Knodel et al.
5,601,224 A 2/1997 Bishop et al.
5,605,272 A 2/1997 Witt et al.
5,607,095 A 3/1997 Smith et al.
5,615,820 A 4/1997 Viola
5,626,587 A 5/1997 Bishop et al.
5,630,539 A 5/1997 Plyley et al.
5,634,584 A 6/1997 Okorocha et al.
5,636,779 A 6/1997 Palmer
5,657,921 A 8/1997 Young et al.
5,662,258 A 9/1997 Knodel et al.
5,662,662 A 9/1997 Bishop et al.
5,662,667 A 9/1997 Knodel
5,673,840 A 10/1997 Schulze et al.
5,673,841 A 10/1997 Schulze et al.
5,673,842 A 10/1997 Bittner et al.
5,676,674 A 10/1997 Bolanos et al.
5,678,748 A 10/1997 Plyley
5,680,982 A 10/1997 Schulze et al.
5,680,983 A 10/1997 Plyley et al.

(56) References Cited

U.S. PATENT DOCUMENTS 5,697,542 A 12/1997 Knodel et al.
5,697,543 A 12/1997 Burdorff
5,704,534 A 1/1998 Huitema et al.
5,704,898 A 1/1998 Kokish
5,706,998 A 1/1998 Blyley et al.
5,709,334 A 1/1998 Sorrentino et al.
5,713,505 A 2/1998 Huitema
5,715,988 A 2/1998 Palmer
5,718,359 A 2/1998 Palmer et al.
5,732,871 A 3/1998 Clark et al.
5,735,445 A 4/1998 Vidal et al.
5,762,255 A 6/1998 Chrisman et al.
5,762,256 A 6/1998 Mastri et al.
5,779,130 A 7/1998 Alesi et al.
5,782,396 A 7/1998 Mastri et al.
5,782,397 A 7/1998 Koukline
5,785,232 A 7/1998 Vidal et al.
5,794,834 A 8/1998 Hamblin et al.
5,797,536 A 8/1998 Smith et al.
5,797,537 A 8/1998 Oberlin et al.
5,797,538 A 8/1998 Heaton et al.
5,810,240 A 9/1998 Robertson
5,814,055 A 9/1998 Knodel et al.
5,820,009 A 10/1998 Melling et al.
5,829,662 A 11/1998 Allen et al.
5,860,995 A 1/1999 Berkelaar
5,865,361 A 2/1999 Milliman et al.
5,878,937 A 3/1999 Green et al.
5,878,938 A 3/1999 Bittner et al.
5,893,506 A 4/1999 Powell
5,894,979 A 4/1999 Powell
5,901,895 A 5/1999 Heaton et al.
5,918,791 A 7/1999 Sorrentino et al.
5,931,847 A 8/1999 Bittner et al.
5,954,259 A 9/1999 Viola et al.
5,964,394 A 10/1999 Robertson
D416,089 S 11/1999 Barton et al.
5,988,479 A 11/1999 Palmer
6,032,849 A 3/2000 Mastri et al.
6,053,390 A 4/2000 Green et al.
6,079,606 A 6/2000 Milliman et al.
6,109,500 A 8/2000 Alli et al.
6,131,789 A 10/2000 Schulze et al.
6,155,473 A 12/2000 Tompkins et al.
D441,865 S 5/2001 Racenet et al.
6,241,139 B1 6/2001 Milliman et al.
6,250,532 B1 6/2001 Green et al.
6,264,087 B1 7/2001 Whitman
6,270,453 B1 8/2001 Sakai
6,325,810 B1 12/2001 Hamilton et al.
6,330,965 B1 12/2001 Milliman et al.
6,488,196 B1 12/2002 Fenton, Jr.
6,550,757 B2 4/2003 Sesek
6,569,171 B2 5/2003 DeGuillebon et al.
6,595,509 B2 7/2003 Sesek
6,619,529 B2 9/2003 Green et al.
6,644,532 B2 11/2003 Green et al.
6,669,073 B2 12/2003 Milliman et al.
6,716,233 B1 4/2004 Whitman
6,786,382 B1 9/2004 Hoffman
6,817,508 B1 11/2004 Racenet et al.
6,821,282 B2 11/2004 Perry et al.
6,835,199 B2 12/2004 McGuckin, Jr. et al.
6,913,181 B2 7/2005 Mochizuki et al.
6,923,360 B2 8/2005 Sesek et al.
6,953,138 B1 10/2005 Dworak et al.
6,953,139 B2 10/2005 Milliman et al.
6,964,363 B2 11/2005 Wales et al.
6,978,921 B2 12/2005 Shelton, IV et al.
6,986,451 B1 1/2006 Mastri et al.
6,988,649 B2 1/2006 Shelton, IV et al.
7,000,818 B2 2/2006 Shelton, IV et al.
7,044,352 B2 5/2006 Shelton, IV et al.
7,044,353 B2 5/2006 Mastri et al.
7,044,947 B2 5/2006 de la Torre et al.
7,055,730 B2 6/2006 Ehrenfels et al.
7,070,083 B2 7/2006 Jankowski
7,097,089 B2 8/2006 Marczyk
7,097,650 B2 8/2006 Weller et al.
7,108,472 B2 9/2006 Norris et al.
7,128,253 B2 10/2006 Mastri et al.
7,140,527 B2 11/2006 Ehrenfels et al.
7,140,528 B2 11/2006 Shelton, IV
7,143,923 B2 12/2006 Shelton, IV et al.
7,143,924 B2 12/2006 Scirica et al.
7,147,139 B2 12/2006 Schwemberger et al.
7,213,736 B2 5/2007 Wales et al.
7,225,964 B2 6/2007 Mastri et al.
7,237,708 B1 7/2007 Guy et al.
7,258,262 B2 8/2007 Mastri et al.
7,275,674 B2 10/2007 Racenet et al.
7,278,562 B2 10/2007 Mastri et al.
7,290,692 B2 11/2007 Marks
7,293,685 B2 11/2007 Ehrenfels et al.
7,303,107 B2 12/2007 Milliman et al.
7,308,998 B2 12/2007 Mastri et al.
7,328,828 B2 2/2008 Ortiz et al.
7,334,717 B2 2/2008 Rethy et al.
7,380,695 B2 6/2008 Doll et al.
7,380,696 B2 6/2008 Shelton, IV et al.
7,398,908 B2 7/2008 Holsten et al.
7,399,310 B2 7/2008 Edoga et al.
7,401,721 B2 7/2008 Holsten et al.
7,404,508 B2 7/2008 Smith et al.
7,407,075 B2 8/2008 Holsten et al.
7,407,078 B2 8/2008 Shelton, IV et al.
7,416,101 B2 8/2008 Shelton, IV et al.
RE40,514 E 9/2008 Mastri et al.
7,419,080 B2 9/2008 Smith et al.
7,419,081 B2 9/2008 Ehrenfels et al.
7,422,136 B1 9/2008 Marczyk
7,422,139 B2 9/2008 Shelton, IV et al.
7,431,188 B1 10/2008 Marczyk
7,434,715 B2 10/2008 Shelton, IV et al.
7,434,716 B2 10/2008 Viola
7,455,208 B2 11/2008 Wales et al.
7,455,676 B2 11/2008 Holsten et al.
7,461,767 B2 12/2008 Viola et al.
7,464,846 B2 12/2008 Shelton, IV et al.
7,464,847 B2 12/2008 Viola et al.
7,464,849 B2 12/2008 Shelton, IV et al.
7,467,740 B2 12/2008 Shelton, IV et al.
7,472,814 B2 1/2009 Mastri et al.
7,472,815 B2 1/2009 Shelton, IV et al.
7,472,816 B2 1/2009 Holsten et al.
7,481,348 B2 1/2009 Marczyk
7,481,349 B2 1/2009 Holsten et al.
7,487,899 B2 2/2009 Shelton, IV et al.
7,490,749 B2 2/2009 Schall et al.
7,506,790 B2 3/2009 Shelton, IV
7,506,791 B2 3/2009 Omaits et al.
7,513,408 B2 4/2009 Shelton, IV et al.
7,530,484 B1 5/2009 Durrani
7,543,730 B1 6/2009 Marczyk
7,543,731 B2 6/2009 Green et al.
7,546,940 B2 6/2009 Milliman et al.
7,549,564 B2 6/2009 Boudreaux
7,552,854 B2 6/2009 Wixey et al.
7,556,186 B2 7/2009 Milliman
7,565,993 B2 7/2009 Milliman et al.
7,568,604 B2 8/2009 Ehrenfels et al.
7,588,174 B2 9/2009 Holsten et al.
7,588,175 B2 9/2009 Timm et al.
7,588,177 B2 9/2009 Racenet
7,604,151 B2 10/2009 Hess et al.
7,611,038 B2 11/2009 Racenet et al.
7,617,961 B2 11/2009 Viola
7,624,902 B2 12/2009 Marczyk et al.
7,631,793 B2 12/2009 Rethy et al.
7,635,074 B2 12/2009 Olson et al.
7,637,409 B2 12/2009 Marczyk
7,637,410 B2 12/2009 Marczyk
7,641,091 B2 1/2010 Olson et al.
7,641,093 B2 1/2010 Doll et al.

(56) References Cited

U.S. PATENT DOCUMENTS 7,641,095 B2 1/2010 Viola
7,644,848 B2 1/2010 Swayze et al.
7,648,055 B2 1/2010 Marczyk
7,651,017 B2 1/2010 Ortiz et al.
7,654,431 B2 2/2010 Hueil et al.
7,658,311 B2 2/2010 Boudreaux
7,665,647 B2 2/2010 Shelton, IV et al.
7,669,746 B2 3/2010 Shelton, IV
7,670,334 B2 3/2010 Hueil et al.
7,673,781 B2 3/2010 Swayze et al.
7,682,367 B2 3/2010 Shah et al.
7,690,547 B2 4/2010 Racenet et al.
7,703,653 B2 4/2010 Shah et al.
7,717,312 B2 5/2010 Beetel
7,721,931 B2 5/2010 Shelton, IV et al.
7,721,933 B2 5/2010 Ehrenfels et al.
7,721,935 B2 5/2010 Racenet et al.
7,721,936 B2 5/2010 Shelton, IV et al.
7,726,538 B2 6/2010 Holsten et al.
7,726,539 B2 6/2010 Holsten et al.
7,731,073 B2 6/2010 Wixey et al.
7,735,703 B2 6/2010 Morgan et al.
7,753,245 B2 7/2010 Boudreaux et al.
7,753,246 B2 7/2010 Scirica
7,757,925 B2 7/2010 Viola et al.
7,766,210 B2 8/2010 Shelton, IV et al.
7,770,774 B2 8/2010 Mastri et al.
7,780,054 B2 8/2010 Wales
7,780,055 B2 8/2010 Scirica et al.
7,784,662 B2 8/2010 Wales et al.
7,784,663 B2 8/2010 Shelton, IV
7,793,812 B2 9/2010 Moore et al.
7,798,386 B2 9/2010 Schall et al.
7,810,693 B2 10/2010 Broehl et al.
7,815,090 B2 10/2010 Marczyk
7,815,091 B2 10/2010 Marczyk
7,819,298 B2 10/2010 Hall et al.
7,819,896 B2 10/2010 Racenet
7,823,760 B2 11/2010 Zemlok et al.
7,828,188 B2 11/2010 Jankowski
7,828,189 B2 11/2010 Holsten et al.
7,837,079 B2 11/2010 Holsten et al.
7,837,081 B2 11/2010 Holsten et al.
7,845,534 B2 12/2010 Viola et al.
7,845,535 B2 12/2010 Scircia
7,845,537 B2 12/2010 Shelton, IV et al.
7,857,184 B2 12/2010 Viola
7,857,185 B2 12/2010 Swayze et al.
7,857,187 B2 12/2010 Milliman
7,861,906 B2 1/2011 Doll et al.
7,866,525 B2 1/2011 Scirica
7,866,527 B2 1/2011 Hall et al.
7,891,534 B2 2/2011 Wenchell et al.
7,905,381 B2 3/2011 Baxter, III et al.
7,909,220 B2 3/2011 Viola
7,909,221 B2 3/2011 Viola et al.
7,913,891 B2 3/2011 Doll et al.
7,914,543 B2 3/2011 Roth et al.
7,918,230 B2 4/2011 Whitman et al.
7,918,376 B1 4/2011 Knodel et al.
7,918,377 B2 4/2011 Measamer et al.
7,922,063 B2 4/2011 Zemlok et al.
7,934,628 B2 5/2011 Wenchell et al.
7,934,629 B2 5/2011 Wixey et al.
7,934,630 B2 5/2011 Shelton, IV et al.
7,942,300 B2 5/2011 Rethy et al.
7,954,685 B2 6/2011 Viola
7,954,686 B2 6/2011 Baxter, III et al.
7,959,050 B2 6/2011 Smith et al.
7,963,433 B2 6/2011 Whitman et al.
7,992,758 B2 8/2011 Whitman et al.
8,002,795 B2 8/2011 Beetel
8,006,887 B2 8/2011 Marczyk
8,007,513 B2 8/2011 Nalagatla et al.
8,008,598 B2 8/2011 Whitman et al.
8,011,550 B2 9/2011 Aranyi et al.
8,011,553 B2 9/2011 Mastri et al.
8,012,170 B2 9/2011 Whitman et al.
8,016,178 B2 9/2011 Olson et al.
8,020,742 B2 9/2011 Marczyk
8,020,743 B2 9/2011 Shelton, IV
8,028,885 B2 10/2011 Smith et al.
8,033,438 B2 10/2011 Scirica
8,033,440 B2 10/2011 Wenchell et al.
8,033,441 B2 10/2011 Marczyk
8,033,442 B2 10/2011 Racenet et al.
8,034,077 B2 10/2011 Smith et al.
8,038,046 B2 10/2011 Smith et al.
8,052,024 B2 11/2011 Viola et al.
8,056,788 B2 11/2011 Mastri et al.
8,056,789 B1 11/2011 White et al.
8,061,576 B2 11/2011 Cappola
8,061,577 B2 11/2011 Racenet et al.
8,070,033 B2 12/2011 Milliman et al.
8,070,034 B1 12/2011 Knodel
8,070,035 B2 12/2011 Holsten et al.
8,070,036 B1 12/2011 Knodel
8,074,861 B2 12/2011 Ehrenfels et al.
8,083,118 B2 12/2011 Milliman et al.
8,087,563 B2 1/2012 Milliman et al.
8,091,753 B2 1/2012 Viola
8,091,754 B2 1/2012 Ehrenfels et al.
8,092,493 B2 1/2012 Marczyk
8,100,309 B2 1/2012 Marczyk
8,113,406 B2 2/2012 Holsten et al.
8,113,407 B2 2/2012 Holsten et al.
8,113,408 B2 2/2012 Wenchell et al.
8,113,410 B2 2/2012 Hall et al.
8,118,207 B2 2/2012 Racenet et al.
8,123,100 B2 2/2012 Holsten et al.
8,127,976 B2 3/2012 Scirica et al.
8,136,712 B2 3/2012 Zingman
8,152,041 B2 4/2012 Kostrzewski
8,157,145 B2 4/2012 Shelton, IV et al.
8,157,150 B2 4/2012 Viola et al.
8,157,152 B2 4/2012 Holsten et al.
8,181,839 B2 5/2012 Beetel
8,186,555 B2 5/2012 Shelton, IV et al.
8,186,556 B2 5/2012 Viola
8,186,560 B2 5/2012 Hess et al.
8,191,752 B2 6/2012 Scirica
8,196,795 B2 6/2012 Moore et al.
8,201,721 B2 6/2012 Zemlok et al.
8,205,619 B2 6/2012 Shah et al.
8,205,780 B2 6/2012 Sorrentino et al.
8,205,781 B2 6/2012 Baxter, III et al.
8,210,411 B2 7/2012 Yates et al.
8,210,416 B2 7/2012 Milliman et al.
8,220,688 B2 7/2012 Laurent et al.
8,225,979 B2 7/2012 Farascioni et al.
8,231,040 B2 7/2012 Zemlok et al.
8,231,041 B2 7/2012 Marczyk et al.
8,235,274 B2 8/2012 Cappola
8,236,010 B2 8/2012 Ortiz et al.
8,240,536 B2 8/2012 Marczyk
8,240,537 B2 8/2012 Marczyk
8,241,322 B2 8/2012 Whitman et al.
8,245,898 B2 8/2012 Smith et al.
8,245,899 B2 8/2012 Swensgard et al.
8,245,900 B2 8/2012 Scirica
8,256,656 B2 9/2012 Milliman et al.
8,272,552 B2 9/2012 Holsten et al.
8,272,554 B2 9/2012 Whitman et al.
8,281,972 B2 10/2012 Wixey et al.
8,281,973 B2 10/2012 Wenchell et al.
8,286,846 B2 10/2012 Smith et al.
8,292,146 B2 10/2012 Holsten et al.
8,292,148 B2 10/2012 Viola
8,292,151 B2 10/2012 Viola
8,292,152 B2 10/2012 Milliman et al.
8,292,153 B2 10/2012 Jankowski
8,292,157 B2 10/2012 Smith et al.
8,308,041 B2 11/2012 Kostrzewski
8,308,043 B2 11/2012 Bindra et al.

(56) References Cited

U.S. PATENT DOCUMENTS 8,317,070 B2 11/2012 Hueil et al.
8,322,455 B2 12/2012 Shelton, IV et al.
8,336,754 B2 12/2012 Cappola et al.
8,342,377 B2 1/2013 Milliman et al.
8,342,378 B2 1/2013 Marczyk et al.
8,342,379 B2 1/2013 Whitman et al.
8,342,380 B2 1/2013 Viola
8,348,125 B2 1/2013 Viola et al.
8,348,129 B2 1/2013 Bedi et al.
8,348,131 B2 1/2013 Omaits et al.
8,353,440 B2 1/2013 Whitman et al.
8,360,297 B2 1/2013 Shelton, IV et al.
8,360,299 B2 1/2013 Zemlok et al.
8,393,513 B2 3/2013 Jankowski
8,397,972 B2 3/2013 Kostrzewski
8,397,973 B1 3/2013 Hausen
8,403,198 B2 3/2013 Sorrentino et al.
8,413,868 B2 4/2013 Cappola
8,414,577 B2 4/2013 Boudreaux et al.
8,418,906 B2 4/2013 Farascioni et al.
8,418,907 B2 4/2013 Johnson et al.
8,418,908 B1 4/2013 Beardsley
8,419,768 B2 4/2013 Marczyk
8,439,246 B1 5/2013 Knodel
8,444,036 B2 5/2013 Shelton, IV
8,453,907 B2 6/2013 Laurent et al.
8,453,912 B2 6/2013 Mastri et al.
8,453,913 B2 6/2013 Milliman
8,459,520 B2 6/2013 Giordano et al.
8,459,522 B2 6/2013 Marczyk
8,464,922 B2 6/2013 Marczyk
8,469,252 B2 6/2013 Holcomb et al.
8,479,967 B2 7/2013 Marczyk
8,496,152 B2 7/2013 Viola
8,496,155 B2 7/2013 Knodel
8,496,156 B2 7/2013 Sniffin et al.
8,496,683 B2 7/2013 Prommersberger et al.
8,505,799 B2 8/2013 Viola et al.
8,505,801 B2 8/2013 Ehrenfels et al.
8,517,239 B2 8/2013 Scheib et al.
8,517,240 B1 8/2013 Mata et al.
8,523,043 B2 9/2013 Ullrich et al.
8,540,130 B2 9/2013 Moore et al.
8,540,133 B2 9/2013 Bedi et al.
8,540,625 B2 9/2013 Miyoshi
8,544,712 B2 10/2013 Jankowski
8,556,151 B2 10/2013 Viola
8,556,152 B2 10/2013 Marczyk et al.
8,556,153 B1 10/2013 Knodel
8,561,871 B2 10/2013 Rajappa et al.
8,561,874 B2 10/2013 Scirica
8,573,459 B2 11/2013 Smith et al.
8,573,460 B2 11/2013 Cappola
8,573,462 B2 11/2013 Smith et al.
8,573,463 B2 11/2013 Scirica et al.
8,573,464 B2 11/2013 Nalagatla et al.
8,579,176 B2 11/2013 Smith et al.
8,579,177 B2 11/2013 Beetel
8,584,919 B2 11/2013 Hueil et al.
8,584,921 B2 11/2013 Scirica
8,596,513 B2 12/2013 Olson
8,608,043 B2 12/2013 Scirica
8,608,045 B2 12/2013 Smith et al.
8,616,427 B2 12/2013 Viola
8,622,274 B2 1/2014 Yates et al.
8,627,992 B2 1/2014 Edoga et al.
8,627,993 B2 1/2014 Smith et al.
8,627,995 B2 1/2014 Smith et al.
8,631,990 B1 1/2014 Park et al.
8,632,525 B2 1/2014 Kerr et al.
8,632,535 B2 1/2014 Shelton, IV et al.
8,636,189 B1 1/2014 Knodel et al.
8,636,190 B2 1/2014 Zemlok et al.
8,636,192 B2 1/2014 Farascioni et al.
8,636,193 B2 1/2014 Whitman et al.
8,636,762 B2 1/2014 Whitman et al.
8,636,766 B2 1/2014 Milliman et al.
8,657,174 B2 2/2014 Yates et al.
8,657,176 B2 2/2014 Shelton, IV et al.
8,657,178 B2 2/2014 Hueil et al.
8,672,209 B2 3/2014 Crainich
8,672,951 B2 3/2014 Smith et al.
8,685,004 B2 4/2014 Zemlock et al.
8,695,865 B2 4/2014 Smith et al.
8,696,665 B2 4/2014 Hunt et al.
8,708,211 B2 4/2014 Zemlok et al.
8,708,213 B2 4/2014 Shelton, IV et al.
8,740,034 B2 6/2014 Morgan et al.
8,740,035 B2 6/2014 Mastri et al.
8,740,036 B2 6/2014 Williams
8,752,748 B2 6/2014 Whitman et al.
8,763,876 B2 7/2014 Kostrzewski
8,770,458 B2 7/2014 Scirica
8,770,459 B2 7/2014 Racenet et al.
8,789,741 B2 7/2014 Baxter, III et al.
8,800,839 B2 8/2014 Beetel
8,800,840 B2 8/2014 Jankowski
8,800,841 B2 8/2014 Ellerhorst et al.
8,806,973 B2 8/2014 Ross et al.
8,807,414 B2 8/2014 Ross et al.
8,820,603 B2 9/2014 Shelton, IV et al.
8,820,608 B2 9/2014 Miyamoto
8,833,631 B2 9/2014 Munro, III et al.
8,840,003 B2 9/2014 Morgan et al.
8,858,571 B2 10/2014 Shelton, IV et al.
8,875,971 B2 11/2014 Hall et al.
8,875,972 B2 11/2014 Weisenburgh, II et al.
8,887,979 B2 11/2014 Mastri et al.
8,899,462 B2 12/2014 Kostrzewski et al.
8,899,463 B2 12/2014 Schall et al.
8,905,288 B2 12/2014 Wenchell
8,920,435 B2 12/2014 Smith et al.
8,925,783 B2 1/2015 Zemlok et al.
8,931,679 B2 1/2015 Kostrzewski
8,931,683 B2 1/2015 Racenet et al.
8,939,343 B2 1/2015 Milliman et al.
8,967,444 B2 3/2015 Beetel
8,967,446 B2 3/2015 Beardsley et al.
8,967,447 B2 3/2015 Hartoumbekis
8,968,276 B2 3/2015 Zemlok et al.
8,973,803 B2 3/2015 Hall et al.
8,979,827 B2 3/2015 Cappola
9,004,340 B2 4/2015 Scirica
9,010,611 B2 4/2015 Ross et al.
9,016,541 B2 4/2015 Viola et al.
9,016,545 B2 4/2015 Aranyi et al.
9,022,271 B2 5/2015 Scirica
9,023,014 B2 5/2015 Chowaniec et al.
9,027,817 B2 5/2015 Milliman et al.
9,027,818 B2 5/2015 Scirica et al.
9,033,202 B2 5/2015 Scirica
9,038,880 B1 5/2015 Donohoe
9,055,943 B2 6/2015 Zemlok et al.
9,072,515 B2 7/2015 Hall et al.
9,084,601 B2 7/2015 Moore et al.
9,101,358 B2 8/2015 Kerr et al.
9,161,813 B2 10/2015 Benamou
9,204,876 B2 12/2015 Cappola et al.
9,237,890 B2 1/2016 Kostrzewski
9,265,585 B2 2/2016 Wingardner et al.
9,282,966 B2 3/2016 Shelton, IV et al.
9,386,984 B2 7/2016 Aronhalt et al.
9,402,629 B2 8/2016 Ehrenfels et al.
9,510,830 B2 12/2016 Shelton, IV et al.
9,532,782 B2 1/2017 Kostrzewski
9,662,108 B2 5/2017 Williams
9,737,302 B2 8/2017 Shelton, IV et al.
9,737,303 B2 8/2017 Shelton, IV et al.
9,797,486 B2 10/2017 Zergiebel et al.
11,311,293 B2 * 4/2022 Roberts ............ A61B 17/07207
12,213,667 B2 * 2/2025 Roberts ............. A61B 17/0686
2002/0025243 A1 2/2002 Heck
2002/0029044 A1 3/2002 Monassevitch et al.
2002/0062136 A1 5/2002 Hillstead

(56) References Cited

U.S. PATENT DOCUMENTS

2002/0120279 A1 8/2002 Deguillebon et al.
2003/0130677 A1 7/2003 Whitman et al.
2004/0006372 A1 1/2004 Racenet et al.
2004/0138705 A1 7/2004 Heino et al.
2005/0234478 A1 10/2005 Wixey
2006/0097026 A1 5/2006 Shelton, IV
2006/0100644 A1 5/2006 Viola
2006/0180634 A1 8/2006 Shelton, IV et al.
2006/0235442 A1 10/2006 Huitema
2006/0289602 A1 12/2006 Wales et al.
2007/0034664 A1 2/2007 Jiang
2007/0039997 A1 2/2007 Mather et al.
2007/0057014 A1 3/2007 Whitman et al.
2007/0068990 A1 3/2007 Shelton, IV et al.
2007/0084897 A1 4/2007 Shelton, IV et al.
2007/0102472 A1 5/2007 Shelton, IV
2007/0119901 A1 5/2007 Ehrenfels et al.
2007/0131732 A1 6/2007 Holsten et al.
2007/0175950 A1 8/2007 Shelton, IV et al.
2007/0175951 A1 8/2007 Shelton, IV et al.
2008/0029574 A1 2/2008 Shelton et al.
2008/0029575 A1 2/2008 Shelton et al.
2008/0041918 A1 2/2008 Holsten et al.
2008/0078807 A1 4/2008 Hess et al.
2008/0083807 A1 4/2008 Beardsley et al.
2008/0169333 A1 7/2008 Shelton et al.
2008/0179375 A1 7/2008 Scirica
2008/0255607 A1 10/2008 Zemlok
2009/0001129 A1 1/2009 Marczyk
2009/0001130 A1 1/2009 Hess et al.
2009/0026245 A1 1/2009 Holsten et al.
2009/0048589 A1 2/2009 Takashino et al.
2009/0057369 A1 3/2009 Smith et al.
2009/0090763 A1 4/2009 Zemlok et al.
2009/0143806 A1 6/2009 Witt et al.
2009/0198272 A1 8/2009 Kerver et al.
2009/0206131 A1 8/2009 Weisenburgh, II et al.
2009/0206133 A1 8/2009 Morgan et al.
2009/0206137 A1 8/2009 Hall et al.
2009/0277948 A1 11/2009 Beardsley et al.
2009/0277949 A1 11/2009 Viola et al.
2010/0069942 A1 3/2010 Shelton, IV
2010/0072258 A1 3/2010 Farascioni et al.
2010/0089970 A1 4/2010 Smith et al.
2010/0193566 A1 8/2010 Scheib et al.
2010/0230465 A1 9/2010 Smith et al.
2010/0331820 A1 12/2010 Prisco et al.
2011/0036892 A1 2/2011 Marczyk et al.
2011/0042440 A1 2/2011 Holsten et al.
2011/0087276 A1 4/2011 Bedi et al.
2011/0108601 A1 5/2011 Clark et al.
2011/0108603 A1 5/2011 Racenet et al.
2011/0121049 A1 5/2011 Malinouskas et al.
2011/0125138 A1 5/2011 Malinouskas et al.
2011/0127185 A1 6/2011 Ward
2011/0139852 A1 6/2011 Zingman
2011/0147433 A1 6/2011 Shelton, IV et al.
2011/0155784 A1 6/2011 Shelton, IV et al.
2011/0155787 A1 6/2011 Laurent et al.
2011/0290851 A1 12/2011 Shelton, IV et al.
2011/0290853 A1 12/2011 Shelton, IV et al.
2012/0061446 A1 3/2012 Knodel et al.
2012/0074198 A1 3/2012 Huitema et al.
2012/0074200 A1 3/2012 Schmid et al.
2012/0078243 A1 3/2012 Worrell et al.
2012/0080482 A1 4/2012 Schall et al.
2012/0080498 A1 4/2012 Shelton, IV et al.
2012/0091182 A1 4/2012 Marczyk
2012/0109186 A1 5/2012 Parrott et al.
2012/0168487 A1 7/2012 Holsten et al.
2012/0193396 A1 8/2012 Zemlok et al.
2012/0203247 A1 8/2012 Shelton, IV et al.
2012/0211542 A1 8/2012 Racenet
2012/0239009 A1 9/2012 Mollere et al.
2012/0253298 A1 10/2012 Henderson et al.
2012/0286022 A1 11/2012 Olson et al.
2012/0318844 A1 12/2012 Shelton, IV et al.
2012/0325893 A1 12/2012 Pastorelli et al.
2013/0001270 A1 1/2013 Kostrzewski
2013/0012958 A1 1/2013 Marczyk et al.
2013/0015229 A1 1/2013 Viola
2013/0015230 A1 1/2013 Wixey et al.
2013/0015232 A1 1/2013 Smith et al.
2013/0015233 A1 1/2013 Viola
2013/0020375 A1 1/2013 Shelton, IV et al.
2013/0037595 A1 2/2013 Gupta et al.
2013/0048697 A1 2/2013 Shelton, IV et al.
2013/0056521 A1 3/2013 Swensgard
2013/0079814 A1 3/2013 Hess et al.
2013/0087603 A1 4/2013 Viola
2013/0092717 A1 4/2013 Marczyk et al.
2013/0098964 A1 4/2013 Smith et al.
2013/0098965 A1 4/2013 Kostrzewski et al.
2013/0098969 A1 4/2013 Scirica et al.
2013/0105545 A1 5/2013 Burbank
2013/0105547 A1 5/2013 Beardsley
2013/0105548 A1 5/2013 Hodgkinson et al.
2013/0105549 A1 5/2013 Holsten et al.
2013/0112730 A1 5/2013 Whitman et al.
2013/0112731 A1 5/2013 Hodgkinson
2013/0126583 A1 5/2013 Hueil et al.
2013/0126586 A1 5/2013 Zhang et al.
2013/0146640 A1 6/2013 Jankowski
2013/0172928 A1 7/2013 Kostrzewski
2013/0172929 A1 7/2013 Hess et al.
2013/0175317 A1 7/2013 Yates et al.
2013/0175322 A1 7/2013 Yates et al.
2013/0184718 A1 7/2013 Smith et al.
2013/0186931 A1 7/2013 Beardsley
2013/0186932 A1 7/2013 Shelton, IV et al.
2013/0186933 A1 7/2013 Shelton, IV et al.
2013/0193188 A1 8/2013 Shelton, IV et al.
2013/0200132 A1 8/2013 Moore et al.
2013/0206816 A1 8/2013 Penna
2013/0214025 A1 8/2013 Zemlok et al.
2013/0221065 A1 8/2013 Aronhalt et al.
2013/0240604 A1 9/2013 Knodel
2013/0248582 A1 9/2013 Scirica
2013/0256370 A1 10/2013 Smith et al.
2013/0256371 A1 10/2013 Shelton, IV
2013/0270321 A1 10/2013 Marczyk
2013/0270323 A1 10/2013 Marczyk
2013/0284789 A1 10/2013 Smith et al.
2013/0284791 A1 10/2013 Olson et al.
2013/0299552 A1 11/2013 Viola
2013/0306702 A1 11/2013 Viola et al.
2013/0306703 A1 11/2013 Ehrenfels et al.
2013/0306706 A1 11/2013 Knodel
2013/0313303 A1 11/2013 Shelton, IV et al.
2013/0327809 A1 12/2013 Shelton, IV et al.
2013/0327810 A1 12/2013 Swayze et al.
2013/0334278 A1 12/2013 Kerr et al.
2013/0334280 A1 12/2013 Krehel et al.
2013/0334281 A1 12/2013 Williams
2013/0334283 A1 12/2013 Swayze et al.
2013/0334284 A1 12/2013 Swayze et al.
2013/0334285 A1 12/2013 Swayze et al.
2013/0334286 A1 12/2013 Swayze et al.
2013/0334287 A1 12/2013 Shelton, IV
2013/0334288 A1 12/2013 Shelton, IV
2014/0014704 A1 1/2014 Onukuri et al.
2014/0014707 A1 1/2014 Onukuri et al.
2014/0021239 A1 1/2014 Kostrzewski
2014/0025046 A1 1/2014 Williams et al.
2014/0027491 A1 1/2014 Beardsley et al.
2014/0027493 A1 1/2014 Jankowski
2014/0042204 A1 2/2014 Beetel
2014/0103092 A1 4/2014 Kostrzewski et al.
2014/0103093 A1 4/2014 Koch, Jr. et al.
2014/0107640 A1 4/2014 Yates et al.
2014/0110453 A1 4/2014 Wingardner et al.
2014/0131416 A1 5/2014 Whitman et al.
2014/0135832 A1 5/2014 Park et al.
2014/0151433 A1 6/2014 Shelton, IV et al.

(56) References Cited

U.S. PATENT DOCUMENTS

2014/0151434 A1 6/2014 Shelton, IV et al.
2014/0158746 A1 6/2014 Mastri et al.
2014/0166727 A1 6/2014 Swayze et al.
2014/0175146 A1 6/2014 Knodel
2014/0175149 A1 6/2014 Smith et al.
2014/0203063 A1 7/2014 Hessler et al.
2014/0205637 A1 7/2014 Widenhouse et al.
2014/0224856 A1 8/2014 Smith et al.
2014/0236173 A1 8/2014 Scirica et al.
2014/0236184 A1 8/2014 Leimbach
2014/0239038 A1 8/2014 Leimbach et al.
2014/0239041 A1 8/2014 Zerkle et al.
2014/0239044 A1 8/2014 Hoffman
2014/0246474 A1 9/2014 Hall et al.
2014/0246475 A1 9/2014 Hall et al.
2014/0246478 A1 9/2014 Baber et al.
2014/0246479 A1 9/2014 Baber et al.
2014/0260746 A1 9/2014 Sakaguchi et al.
2014/0263537 A1 9/2014 Leimbach et al.
2014/0263539 A1 9/2014 Leimbach et al.
2014/0263541 A1 9/2014 Leimbach et al.
2014/0263542 A1 9/2014 Leimbach et al.
2014/0263543 A1 9/2014 Leimbach et al.
2014/0263545 A1 9/2014 Williams et al.
2014/0263546 A1 9/2014 Aranyi
2014/0263550 A1 9/2014 Aranyi et al.
2014/0263553 A1 9/2014 Leimbach et al.
2014/0263554 A1 9/2014 Leimbach et al.
2014/0263555 A1 9/2014 Hufnagel et al.
2014/0263559 A1 9/2014 Williams et al.
2014/0263562 A1 9/2014 Patel et al.
2014/0263564 A1 9/2014 Leimbach et al.
2014/0263565 A1 9/2014 Lytle, IV et al.
2014/0263566 A1 9/2014 Williams et al.
2014/0263567 A1 9/2014 Williams et al.
2014/0263568 A1 9/2014 Williams et al.
2014/0263569 A1 9/2014 Williams et al.
2014/0263570 A1 9/2014 Hopkins et al.
2014/0263571 A1 9/2014 Morgan et al.
2014/0263572 A1 9/2014 Shelton, IV et al.
2014/0284372 A1 9/2014 Kostrzewski
2014/0291378 A1 10/2014 Shelton, IV et al.
2014/0299649 A1 10/2014 Shelton, IV et al.
2014/0305986 A1 10/2014 Hall et al.
2014/0305988 A1 10/2014 Boudreaux et al.
2014/0305992 A1 10/2014 Kimsey et al.
2014/0305994 A1 10/2014 Parihar et al.
2014/0353359 A1 12/2014 Hall et al.
2015/0008248 A1 1/2015 Giordano et al.
2015/0034697 A1 2/2015 Mastri et al.
2015/0041518 A1 2/2015 Shelton, IV et al.
2015/0053738 A1 2/2015 Morgan et al.
2015/0053740 A1 2/2015 Shelton, IV
2015/0053741 A1 2/2015 Shelton, IV et al.
2015/0053742 A1 2/2015 Shelton, IV et al.
2015/0053743 A1 2/2015 Yates et al.
2015/0053744 A1 2/2015 Swayze et al.
2015/0053745 A1 2/2015 Yates et al.
2015/0053746 A1 2/2015 Shelton, IV et al.
2015/0053748 A1 2/2015 Yates et al.
2015/0053749 A1 2/2015 Shelton, IV et al.
2015/0054753 A1 2/2015 Morgan et al.
2015/0060516 A1 3/2015 Collings et al.
2015/0060517 A1 3/2015 Williams
2015/0060521 A1 3/2015 Weisenburgh, II et al.
2015/0076205 A1 3/2015 Zergiebel
2015/0076206 A1 3/2015 Sapre
2015/0076209 A1 3/2015 Shelton, IV et al.
2015/0076210 A1 3/2015 Shelton, IV et al.
2015/0076212 A1 3/2015 Shelton, IV
2015/0083781 A1 3/2015 Giordano et al.
2015/0083783 A1 3/2015 Shelton, IV et al.
2015/0090760 A1 4/2015 Giordano et al.
2015/0090761 A1 4/2015 Giordano et al.
2015/0090762 A1 4/2015 Giordano et al.
2015/0090764 A1 4/2015 Zemlok et al.
2015/0108201 A1 4/2015 Williams
2015/0122872 A1 5/2015 Olson et al.
2015/0127046 A1 5/2015 Peterson
2015/0129631 A1 5/2015 Beetel
2015/0129634 A1 5/2015 Shelton, IV et al.
2015/0133995 A1 5/2015 Shelton, IV et al.
2015/0133996 A1 5/2015 Shelton, IV et al.
2015/0134076 A1 5/2015 Shelton, IV et al.
2015/0144678 A1 5/2015 Hall et al.
2015/0201935 A1 7/2015 Weisenburgh, II et al.
2015/0208902 A1 7/2015 Okamoto
2015/0245834 A1 9/2015 Scirica et al.
2015/0272576 A1* 10/2015 Cappola ............... A61B 17/072 227/175.2
2015/0289873 A1 10/2015 Shelton, IV et al.
2015/0297221 A1 10/2015 Kerr et al.
2015/0297233 A1 10/2015 Huitema et al.
2015/0374363 A1* 12/2015 Laurent, IV ......... A61B 17/105 227/176.1
2015/0380187 A1 12/2015 Zergiebel et al.
2016/0000439 A1 1/2016 Weisenburgh, II et al.
2016/0000440 A1 1/2016 Weisenburgh, II et al.
2016/0058447 A1 3/2016 Posada et al.
2016/0058492 A1 3/2016 Yates et al.
2016/0183948 A1 6/2016 Shelton, IV et al.
2016/0310204 A1 10/2016 McHenry et al.
2016/0338702 A1 11/2016 Ehrenfels et al.
2016/0374672 A1 12/2016 Bear et al.
2016/0374675 A1 12/2016 Shelton, IV et al.
2017/0007241 A1 1/2017 Shelton, IV et al.
2017/0007242 A1 1/2017 Shelton, IV et al.
2017/0007243 A1 1/2017 Shelton, IV et al.
2017/0007249 A1 1/2017 Shelton, IV et al.
2017/0231633 A1* 8/2017 Marczyk ................ A61B 17/32 227/175.2
2017/0245856 A1 8/2017 Baxter, III et al.
2017/0245858 A1 8/2017 Williams
2017/0281161 A1 10/2017 Shelton, IV et al.
2017/0281165 A1 10/2017 Harris et al.
2017/0281168 A1 10/2017 Shelton, IV et al.
2017/0290583 A1 10/2017 Reed et al.
2017/0290584 A1* 10/2017 Jasemian ............. A61B 17/072
2019/0150919 A1* 5/2019 Williams ............. A61B 17/105
2019/0183503 A1* 6/2019 Shelton, IV ........... A61B 90/06
2019/0261984 A1 8/2019 Nelson et al.
2020/0268381 A1 8/2020 Roberts et al.

FOREIGN PATENT DOCUMENTS

EP 0 514 139 A2 11/1992
EP 0 536 903 A2 4/1993
EP 0 596 543 A1 5/1994
EP 1 523 944 A1 4/2005
EP 1 759 812 A1 3/2007
EP 1 915 953 A1 4/2008
EP 1 479 348 B1 7/2008
EP 2 044 893 A2 9/2008
EP 2 005 902 A2 12/2008
EP 2 090 241 A1 8/2009
EP 2 263 568 A2 12/2010
EP 2 361 562 A1 8/2011
EP 2 462 875 A2 6/2012
EP 2 486 859 A2 8/2012
EP 2 764 833 A2 8/2014
EP 2 772 192 A1 9/2014
EP 2 777 530 A1 9/2014
EP 2 815 705 A1 12/2014
EP 2 923 661 A2 3/2015
EP 2 853 204 A1 4/2015
EP 2 891 462 A1 7/2015
EP 2 926 742 A1 10/2015
EP 2 942 020 A2 11/2015
EP 2 959 841 A1 12/2015
EP 3 135 225 A2 3/2017
EP 3 238 639 A2 3/2017
EP 3 338 653 A1 6/2018
EP 3 338 698 A1 6/2018
EP 3 338 702 A1 6/2018

(56) References Cited

FOREIGN PATENT DOCUMENTS

| | | | |
|---|---|---|---|
| JP | 2001-087272 | A | 4/2001 |
| RU | 2063710 | | 7/1996 |
| WO | WO 83/02247 | A1 | 7/1983 |
| WO | WO 94/24947 | A1 | 11/1994 |
| WO | WO 02/30296 | A2 | 4/2002 |
| WO | WO 02/096327 | A2 | 12/2002 |
| WO | WO 2003/094747 | A1 | 11/2003 |
| WO | WO 2004/032762 | A1 | 4/2004 |
| WO | WO 2012/052729 | A1 | 4/2012 |
| WO | WO 2014/139440 | A1 | 9/2014 |
| WO | WO 2020/077531 | A1 | 4/2020 |
| WO | WO 2021/124010 | A1 | 6/2021 |

OTHER PUBLICATIONS

Ethicon Endo Surgery, Inc., Contour Curved Cutter Stapler, 2014, 2 pgs.

JustRight Surgical, JustRight Surgery, Dec. 31, 2014, 2 pgs.

European Patent Office, The International Search Report and the Written Opinion of the International Searching Authority for International Application No. PCT/US2014/028811, entitled "Surgical Stapler Having Actuation Mechanism with Rotatable Shaft," mailed Aug. 5, 2014, 14 pgs.

European Patent Office, International Search Report and Written Opinion for International Application No. PCT/US2014/028211, entitled "Surgical Stapler with Partial Pockets," mailed Sep. 8, 2014, 17 pgs.

International Searching Authority, U.S., The International Search Report and the Written Opinion of the International Searching authority for international application PCT/US2014/027768, titled "Surgical Stapler with Expandable Jaw", mailed Jul. 25, 2014, 17 pgs.

The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.

International Searching Authority, U.S., The International Search Report and the Written Opinion of the International Searching authority for international application PCT/US2015/0035379, titled "Surgical Stapler with Circumferential Firing", mailed Sep. 15, 2015, 22 pgs.

The International Bureau of WIPO, International Preliminary Report on Patentability, for International Application No. PCT/US2014/027768, entitled "Surgical Stapler with Expandable Jaw," dated Sep. 24, 2015, 9 pgs.

European Patent Office, International Search Report and Written Opinion for International Application No. PCT/US2015/050103 titled "Surgical Stapler with Self-Adjusting Staple Height" dated Feb. 17, 2016, 18 pgs.

The International Bureau of WIPO, International Preliminary Report on Patentability for International Application No. PCT/US2015/035379, entitled "Surgical Stapler with Circumferential Firing," dated Dec. 22, 2016, 14 pgs.

The International Bureau of WIPO, International Preliminary Report on Patentability for International Application No. PCT/US2015/050103, titled "Surgical Stapler With Self-Adjusting Staple Height," dated Mar. 30, 2017, 12 pgs.

European Patent Office, European Search Report for European Application No. EP14764812.5, entitled "Surgical Stapler Having Actuation Mechanism with Rotatable Shaft," dated Apr. 6, 2017, 6 pgs.

International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.

International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.

International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.

European Patent Office, The International Search Report and the Written Opinion of the International Searching Authority for International Application No. PCT/US2017/027269, entitled "Reload Shaft Assembly for Surgical Stapler," mailed Sep. 12, 2017, 22 pgs.

European Patent Office, The International Search Report and the Written Opinion of the International Searching Authority for International Application No. PCT/US2017/027213, entitled "Surgical Stapler Having a Powered Handle," mailed Sep. 13, 2017, 17 pgs.

European Patent Office, The International Search Report and the Written Opinion of the International Searching Authority for International Application No. PCT/US2017/027142, entitled "Surgical Stapler Having Articulation Mechanism," mailed Sep. 14, 2017, 21 pgs.

European Patent Office, The International Search Report and Written Opinion of the International Searching Authority for International Application No. PCT/US2016/045993 titled "Surgical Stapler Having Locking Articulation Joint", mailed Jan. 24, 2017, 20 pgs.

European Patent Office, Partial European Search Report for European Application No. EP 14762896.0, entitled "Surgical Stapler with Expandable Jaw," dated Apr. 10, 2017, 6 pgs.

The International Bureau of WIPO, International Preliminary Report on Patentability, for International Application No. PCT/US2016/045993, entitled "Surgical Stapler Having Locking Articulation Joint," dated Feb. 15, 2018, 13 pgs.

European Patent Office, Extended European Search Report for European Application No. EP 18186558.5, entitled "Surgical Stapler with Partial Pockets," dated Oct. 10, 2018, 9 pgs.

The International Bureau of WIPO, International Preliminary Report on Patentability, for International Application No. PCT/US2017/027142, entitled "Surgical Stapler Having Articulation Mechanism," dated Oct. 25, 2018, 12 pgs.

The International Bureau of WIPO, International Preliminary Report on Patentability, for International Application No. PCT/US2017/027213, entitled "Surgical Stapler Having Powered Handle," dated Oct. 25, 2018, 9 pgs.

The International Bureau of WIPO, International Preliminary Report on Patentability, for International Application No. PCT/US2017/027269, entitled "Reload Shaft Assembly for Surgical Stapler," dated Oct. 25, 2018, 12 pgs.

European Patent Office, Extended European Search Report for European Application No. EP 18189960.0, entitled "Surgical Stapler with Expandable Jaw," dated Dec. 13, 2018, 6 pgs.

International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.

European Patent Office, The International Search Report and the Written Opinion of the International Searching Authority for International Application No. PCT/US2019/019867, entitled "Surgical Stapler Having a Powered Handle," mailed Jul. 19, 2019, 24 pgs.

European Patent Office, Extended European Search Report for European Application No. EP 19150575.9, entitled "Surgical Stapler Having Actuation Mechanism with Rotatable Shaft," dated Aug. 21, 2019, 5 pgs.

European Patent Office, Extended European Search Report for European Application No. EP 19180055.6, entitled "Surgical Stapler with Circumferential Firing," dated Sep. 20, 2019, 8 pgs.

European Patent Office, The International Search Report and the Written Opinion of the International Searching Authority for International Application No. PCT/US2020/019938, entitled "Surgical Stapling Instrument Having a Two-Position Mechanism," mailed Jun. 18, 2020, 16 pgs.

European Patent Office, Extended European Search Report for European Application No. EP 20157713.7, entitled "Surgical Stapler with Expandable Jaw," dated May 11, 2020, 6 pgs.

International Searching Authority/ EPO, Invitation to Pay Additional Fees for PCTUS2020/025496, entitled "Reload Cover for Surgical Stapling System," dated Jun. 18, 2019, 15 pgs.

(56) References Cited

OTHER PUBLICATIONS

European Patent Office, Extended European Search Report for European Application No. EP 20161294.2, entitled "Surgical Stapler with Self-Adjusting Staple Height," dated Jun. 22, 2020, 6 pgs.
European Patent Office, The International Search Report and the Written Opinion of the International Searching Authority for International Application No. PCT/US2020/025496, entitled "Reload Cover for Surgical Stapling System," mailed Aug. 13, 2020, 20 pgs.
The International Bureau of WIPO, International Preliminary Report on Patentability, for International Application No. PCT/US2019/019867, entitled "Surgical Stapler Having a Powered Handle," dated Sep. 3, 2020, 16 pgs.
European Patent Office, Extended European Search Report for European Application No. EP 20197859.0, entitled "Surgical Stapler with Circumferential Firing," dated Jan. 28, 2021, 13 pgs.
European Patent Office, The International Search Report and Written Opinion for International Application No. PCT/US2020/067540, mailed May 3, 2021, entitled "Electrosurgical System with Tissue and Maximum Current Identification," 12 pages.
European Patent Office, Extended European Search Report for European Application No. EP 21162419.2, entitled "Surgical Stapler Having Articulation Mechanism," dated Jun. 22, 2021, 10 pgs.
The International Bureau of WIPO, International Preliminary Report on Patentability, for International Application No. PCT/US2020/019938, entitled "Surgical Stapler Having a Two-Position Lockout Mechanism," dated Sep. 10, 2020, 10 pgs.
The International Bureau of WIPO, International Preliminary Report on Patentability, for International Application No. PCT/US2020/025496 entitled "Reload Cover for Surgical System," dated Oct. 14, 2021, 12 pgs.
European Patent Office, Extended European Search Report for European Application No. EP 21173771.3, entitled "Reload Shaft Assembly for Surgical Stapler," dated Aug. 27, 2021, 10 pgs.
European Patent Office, Extended European Search Report for European Application No. EP 21195788.1, entitled "Surgical Stapler with Self-Adjusting Staple Height," dated Dec. 13, 2021, 9 pgs.
International Searching Authority/ EPO, Invitation to Pay Additional Fees and Communication Relating to the Results of the Partial International Search for PCT/US2021/057365, entitled "Surgical Stapler Having a Powered Handle," dated Feb. 23, 2022, 14 pgs.
European Patent Office, The International Search Report and the Written Opinion of the International Searching Authority for International Application No. PCT/US2021/057278, entitled "Actuation Shaft Retention Mechanism for Surgical Stapler" mailed Feb. 23, 2022, 15 pgs.
European Patent Office, The International Search Report and the Written Opinion of the International Searching Authority for International Application No. PCT/US2021/057231, entitled "Material Combinations and Processing Methods for a Surgical Instrument" mailed Feb. 11, 2022, 15 pgs.
European Patent Office, The International Search Report and the Written Opinion of the International Searching Authority for International Application No. PCT/US2021/057365, entitled "Surgical Stapler Having a Powered Handle" mailed Apr. 13, 2022, 21 pgs.
European Patent Office, The International Search Report and the Written Opinion of the International Searching Authority for International Application No. PCT/US2022/012452, entitled "Surgical Stapler Having Shaft Recognition Mechanism" mailed Apr. 13, 2022, 13 pgs.
International Preliminary Examining Authority/US, International Preliminary Report on Patentability for International Application No. PCT/US2020/067540, titled "Electrosurgical System with Tissue and Maximum Current Identification," dated Jul. 14, 2022, 9 pgs.
European Patent Office, Extended European Search Report for European Application No. EP 22196603.9, entitled "Surgical Stapler with Expandable Jaw," dated Dec. 14, 2022, 6 pgs.
European Patent Office, Extended European Search Report for European Application No. EP 22203464.7, entitled "Surgical Stapler with Partial Pockets," dated Dec. 20, 2022, 9 pgs.
European Patent Office, Extended European Search Report for European Application No. EP 22203599.0, entitled "Surgical Stapler Having a Powered Handle," dated Feb. 7, 2023, 7 pgs.
The International Bureau of WIPO, International Preliminary Report on Patentability, for International Application No. PCT/US2021/057231, entitled "Material Combinations and Processing Methods for a Surgical Instrument," dated May 11, 2023, 10 pgs.
The International Bureau of WIPO, International Preliminary Report on Patentability, for International Application No. PCT/US2021/057278, entitled "Actuation Shaft Retention Mechanism for Surgical Stapler," dated May 11, 2023, 10 pgs.
The International Bureau of WIPO, International Preliminary Report on Patentability, for International Application No. PCT/US2021/057365, entitled "Surgical Stapler Having a Powered Handle," dated May 11, 2023, 14 pgs.
The International Bureau of WIPO, International Preliminary Report on Patentability, for International Application No. PCT/US2022/012452, entitled "Surgical Stapler Having Shaft Recognition Mechanism," dated Jul. 27, 2023, 8 pgs.
European Patent Office, Extended European Search Report for European Application No. EP 23185918.2, entitled "Surgical Stapler Having Actuation Mechanism with Rotatable Shaft," dated Sep. 22, 2023, 5 pgs.
European Patent Office, Extended European Search Report for European Application No. EP 23198045.9, entitled "Reload Shaft Assembly for Surgical Stapler," dated Oct. 25, 2023, 12 pgs.
European Patent Office, Partial Extended European Search Report for European Patent Application No. 23198488.1, titled "Surgical Stapler with Self-Adjusting Staple Height," dated Jan. 23, 2024, 8 pgs.
European Patent Office, Extended European Search Report for European Application No. EP 25188896.2, entitled "Surgical Stapling Instrument Having a Two-Position Lockout Mechanism," dated Oct. 17, 2025, 12 pgs.

* cited by examiner

L
22
20

30
24
36
34
32
50

SURGICAL STAPLING INSTRUMENT HAVING A TWO-POSITION LOCKOUT MECHANISM

CROSS-REFERENCE TO RELATED APPLICATIONS

This application is a continuation of U.S. patent application Ser. No. 18/364,968 entitled "Surgical Stapling Instrument Having a Two-Position Lockout Mechanism" filed on Aug. 3, 2023, which is a continuation of U.S. patent application Ser. No. 17/700,789 entitled "Surgical Stapling Instrument Having a Two-Position Lockout Mechanism" filed on Mar. 22, 2022, now U.S. Pat. No. 11,751,871, which is a continuation of U.S. patent application Ser. No. 16/801,788 entitled "Surgical Stapling Instrument Having a Two-Position Lockout Mechanism" filed on Feb. 26, 2020, now U.S. Pat. No. 11,311,293, which claims priority to and benefit of U.S. Provisional Patent Application Ser. No. 62/811,457 entitled "Surgical Stapling Instrument Having a Two-Position Lockout Mechanism" filed on Feb. 27, 2019, each of which is incorporated herein by reference in its entirety.

BACKGROUND OF THE INVENTION

Field of the Invention

The present application relates generally to surgical occlusion instruments and, more particularly, to surgical staplers.

Description of the Related Art

Surgical staplers are used to approximate or clamp tissue and to staple the clamped tissue together. As such, surgical staplers have mechanisms to ensure that tissue is properly positioned and captured and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

Surgical staplers can further include cutting blades that transect tissue being stapled. These staplers can have mechanisms to restrict motion of the cutting blades when no staples are present in the device. Further improvements of mechanisms to restrict motion of the cutting blade of a surgical stapler are desirable to enhance user tactile experience and patient safety in certain stapler configurations.

SUMMARY OF THE INVENTION

In certain embodiments, a surgical stapling device is provided herein. The surgical stapling device comprises an elongate shaft, a firing beam, and a jaw assembly. The elongate shaft has a proximal end, a distal end, and a longitudinal axis extending between the proximal end and the distal end. The firing beam has a proximal end and a distal end. At least a portion of the firing beam is longitudinally slidable within the elongate shaft. The firing member is at the distal end of the firing beam. The jaw assembly is at the distal end of the elongate shaft. The jaw assembly comprises a first jaw, a second jaw, an empty jaw assembly lockout mechanism, and a fired reload lockout mechanism. The first jaw defines an anvil. The second jaw defines a reload support configured to receive a reload cartridge having a plurality of staples deployable therefrom. The first jaw is pivotably coupled to the second jaw. The firing member is longitudinally slidable within the jaw assembly to move the jaw assembly in an open close stroke to pivot the first jaw relative to the second jaw from an open configuration to a closed configuration and in a firing stroke distal the open close stroke to fire staples from the reload cartridge. The empty jaw assembly lockout mechanism restricts distal movement of the firing member in the open close stroke when no reload cartridge is present in the reload support. The fired reload lockout mechanism prevents distal movement of the firing member from the open close stroke to the firing stroke.

In certain embodiments, a surgical stapler is provided herein. The surgical stapler comprises an elongate shaft, a firing beam, a firing member, and a jaw assembly. The elongate shaft has a proximal end, a distal end, and a longitudinal axis extending between the proximal end and the distal end. The firing beam has a proximal end and a distal end. At least a portion of the firing beam is longitudinally slidable within the elongate shaft. The firing beam comprising a first notch formed therein and a second notch formed therein. The firing member is at the distal end of the firing beam. The jaw assembly is at the distal end of the elongate shaft. The jaw assembly comprises a first jaw, a second jaw, and a lockout lever. The first jaw defines an anvil. The second jaw defines a reload support configured to receive a reload cartridge having a plurality of staples deployable therefrom. The lockout lever is pivotably coupled to the second jaw. The lockout lever has a proximal end, a distal end, and a pivot between the proximal end and the distal end. The lockout lever is pivotable between a first position in which the proximal end of the lockout lever is at a first height corresponding to the first notch, a second position in which the proximal end of the lockout lever is at a second height corresponding to a position of the second notch, and an unlocked position in which the proximal end of the lockout lever is at a third height spaced apart from the first notch and the second notch.

In certain embodiments, a surgical stapler is provided herein. The surgical stapler comprises an elongate shaft, a firing beam, a firing member, and a jaw assembly. The elongate shaft has a proximal end, a distal end, and a longitudinal axis extending between the proximal end and the distal end. The firing beam has a proximal end and a distal end. At least a portion of the firing beam is longitudinally slidable within the elongate shaft. The firing beam comprises a first notch formed therein and a second notch formed therein. The firing member is at the distal end of the firing beam. The jaw assembly is at the distal end of the elongate shaft. The jaw assembly comprises a first jaw, a second jaw, a first lockout lever, and a second lockout lever. The first jaw defines an anvil. The second jaw defines a reload support configured to receive a reload cartridge having a plurality of staples deployable therefrom. The first lockout lever is pivotably coupled to the second jaw. The first lockout lever has a proximal end, a distal end, and a pivot between the proximal end and the distal end. The second lockout lever is pivotably coupled to the second jaw. The second lockout lever has a proximal end, a distal end, and a pivot between the proximal end and the distal end. The first lockout lever is pivotable between a first position in which the proximal end of the first lockout lever is at a first height spaced apart from the first notch and a second position in which the proximal end of the lockout lever is at a second height corresponding to a position of the first notch. The second lockout lever is pivotable between a first position in which the proximal end of the second lockout lever is at a first height spaced apart from the second notch and a second position in which the proximal end of the lockout lever is at a second height corresponding to a position of the second notch.

DETAILED DESCRIPTION OF THE INVENTION

Figure 1:
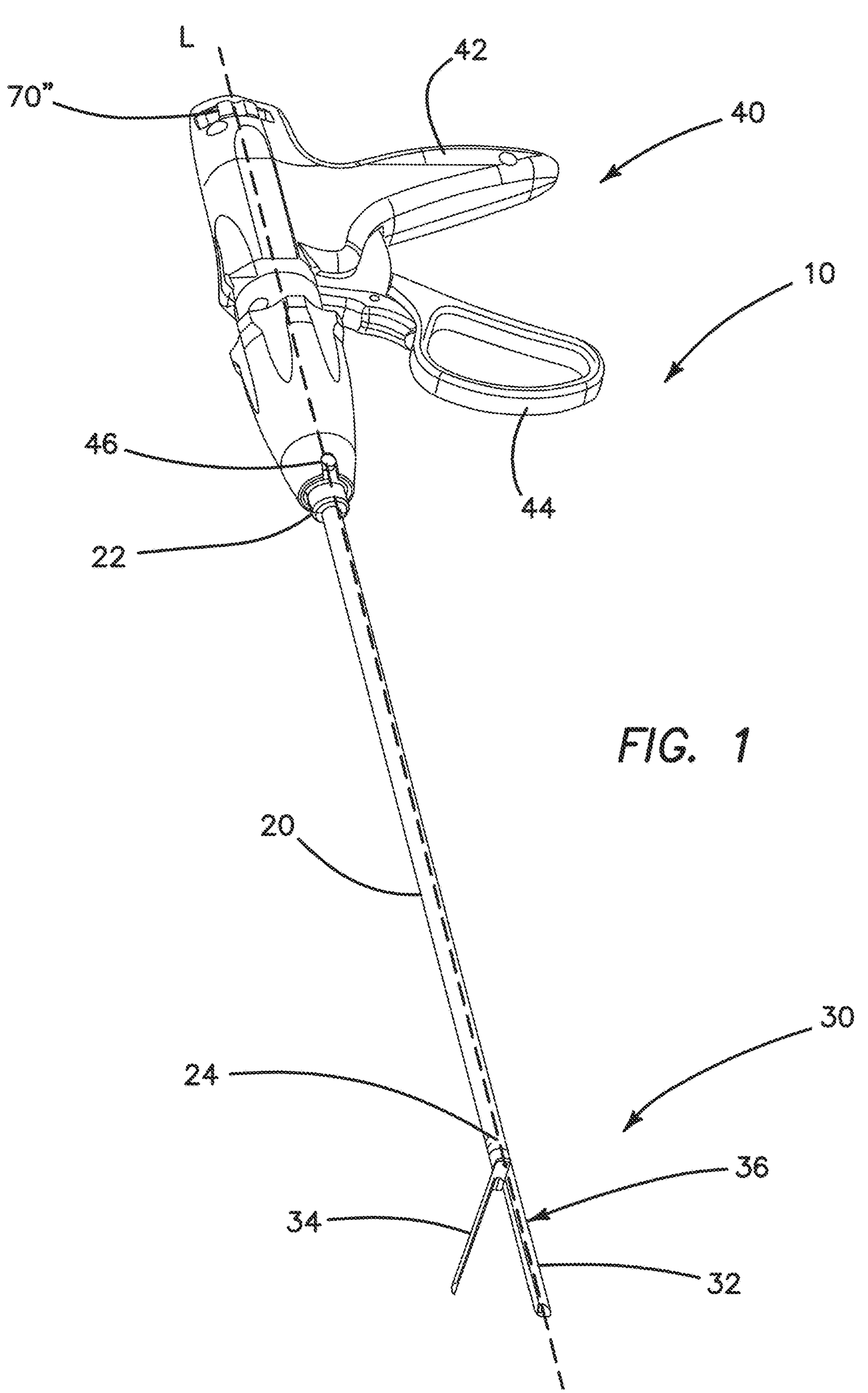
FIG. 1 is a perspective view of an embodiment of surgical stapling device with the jaws in an open configuration.
Figure 2:
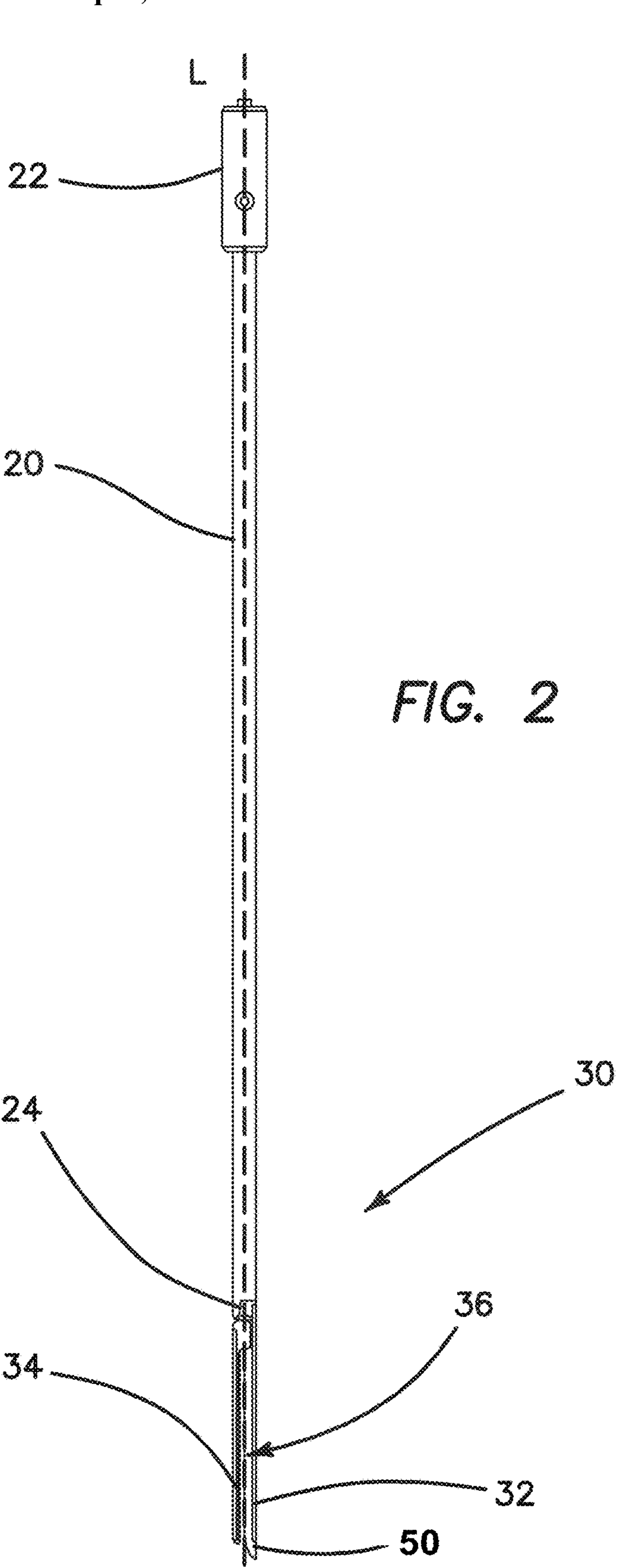
FIG. 2 is a perspective view of an embodiment of a reload shaft for the surgical stapling device of FIG. 1 with the jaws in a closed configuration.

With reference to FIGS. 1-5, embodiments of surgical stapling device are illustrated. The embodiment of stapling device illustrated in FIGS. 1-3 includes a mechanical handle assembly 40, and the embodiment of stapling device illustrated in FIGS. 4-5 includes an electrically powered handle assembly 40'. The illustrated embodiment of surgical stapler 10 comprises an elongate shaft 20, a jaw assembly 30, and a handle assembly 40, 40'. Various aspects of the elongate shaft 20 and jaw assembly 30 described herein can be used interchangeably with either the mechanical handle assembly 40 or the powered handle assembly 40'. FIG. 1 illustrates the surgical stapler 10 with the jaw assembly 30 in an open configuration. FIG. 2 illustrates a removable reload shaft assembly comprising the elongate shaft 20 and jaw assembly 30 of the surgical stapler 10 with the jaw assembly 30 in a closed configuration.

With continued reference to FIGS. 1 and 2, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIGS. 1 and 2, as illustrated, the elongate shaft 20 comprises a generally tubular member. The elongate shaft 20 extends from a proximal end 22 to a distal end 24. The elongate shaft 20 defines a central longitudinal axis, L. of the surgical stapler 10 extending between the proximal end 22 and the distal end 24.

With continued reference to FIGS. 1 and 2, in the illustrated embodiment, the jaw assembly 30 is coupled to the elongate shaft 20 at the distal end 24 of the elongate shaft 20. The jaw assembly 30 comprises a first jaw 34 pivotally coupled to a second jaw 32. In the embodiment illustrated in FIGS. 1-2, the jaw assembly is fixed in an orientation longitudinally aligned with the central longitudinal axis L. In other embodiments, elongate shafts can include jaw assemblies articulably coupled to the elongate shaft such that the jaw assembly can be selectively positioned at an articulated position with respect to the central longitudinal axis L. The handle assembly of FIG. 3 includes an articulation knob 190 and articulation mechanism configured to provide continuously selectable articulation of a jaw assembly of an elongate shaft assembly through an articulation range. In an initial configuration, the second jaw 32 includes a plurality of staples 36 disposed therein.

With continued reference to FIGS. 1 and 2, in the illustrated embodiment, the jaw assembly 30 can be actuated from an open configuration (FIG. 1) to a closed configuration (FIG. 2) to a stapling configuration by an actuation member or beam that is longitudinally slidable within the elongate shaft. In an initial position, the beam can be positioned at the distal end 24 of the elongate shaft 20. With the beam in the initial position, the first jaw 34 is pivoted away from the second jaw 32 such that the jaw assembly 30 is in the open configuration. The actuation beam engages the first jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the second jaw 32 such that further translation of the actuation beam distally past the first distance deploys the plurality of staples 36 from the second jaw 32.

Figure 3:
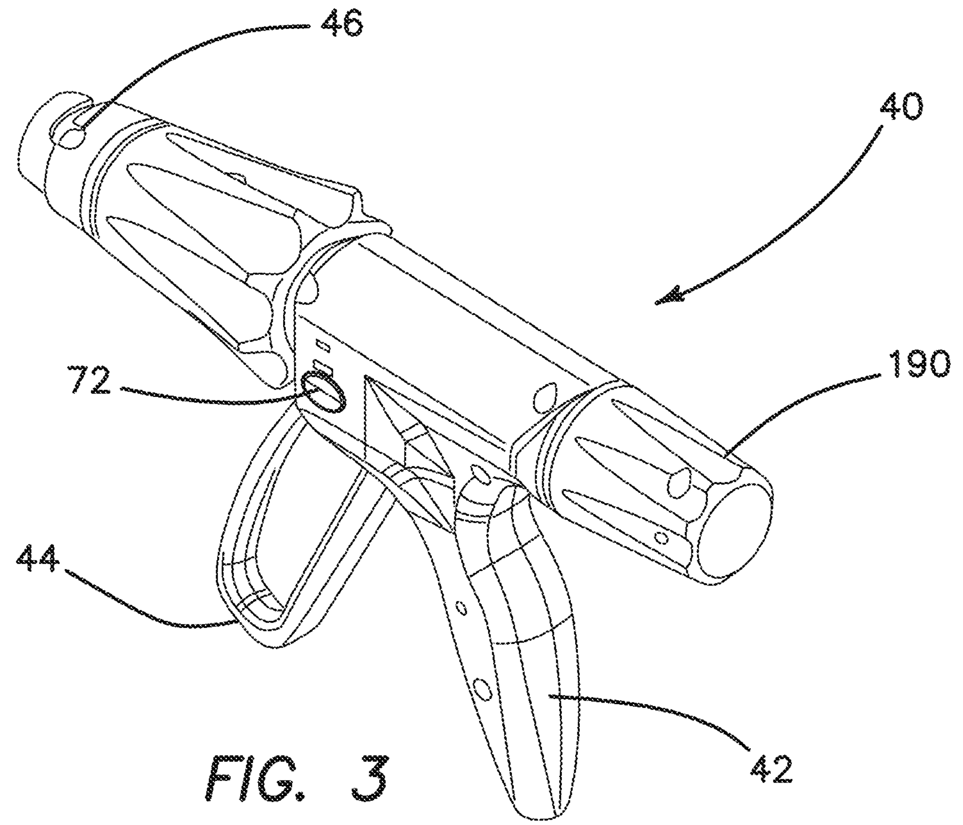
FIG. 3 is a perspective view of an embodiment of handle assembly having an articulation mechanism for a surgical stapling device.

With reference to FIGS. 1-3, in the illustrated embodiment, the handle assembly is coupled to the elongate shaft 20 at the proximal end 22 of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configurations such as, for example, scissors-grip configurations, or in-line configurations. The handle assembly 40 houses an actuation mechanism configured to selectively advance an actuation shaft responsive to movement of the movable handle 44 to actuate the actuation beam within the elongate a shaft a first distance in an open-close stroke to close the jaw assembly from an initial open position, a second distance beyond the first distance in a firing stroke to fire staples, and to return the actuation beam the second distance and the first distance to an initial position. In certain embodiments, a sliding selector 72 on the handle assembly can allow a user to select whether the handle assembly operates to actuate a jaw assembly in an open-close stroke or a firing stroke. Various embodiments of handle assemblies and associated actuation mechanisms are disclosed in U.S. Pat. No. 9,668,732, entitled "Surgical Stapler Handle Assembly Having Actuation Mechanism With Longitudinally Rotatable Shaft" and U.S. patent application Ser. No. 15/485,620, filed Apr. 12, 2017, entitled "Surgical Stapler Having Articulation Mechanism," both of which are incorporated by reference herein in their entireties.

With reference to FIG. 2, in some embodiments, the surgical stapler 10 can include the plurality of staples 36 positioned in a disposable reload cartridge 50 while the handle assembly 40 and elongate shaft 20 is configured to be reused with multiple staple reload cartridges. Advantageously, the grasping and firing lockout mechanisms described herein can limit functionality of the handle assembly to alert a user and enhance patient safety if no reload cartridge is present in the jaw assembly or if a partially or fully fired reload cartridge is present in the jaw assembly. In the illustrated embodiment of FIG. 1, the elongate shaft 20 and jaw assembly 30 define a reusable shaft assembly that is removably couplable to the handle assembly 40. Various aspects of the lockout mechanisms described herein can be used by the shaft assembly and one or more disposable cartridge thereof to limit functionality of the handle assembly after partial or complete firing of the staples from the jaw assembly.

With reference to FIG. 3, the handle assembly 40 includes a coupler 46 at the distal end thereof. The coupler 46 is adapted to engage the elongate shaft 20 of the surgical stapler 10 The coupler 46 can have a bayonet connection having an outer connector that can removably couple the handle assembly 40 to the elongate shaft 20, and an inner connector that can removably couple the actuation shaft of the handle assembly 42 to the actuation member of the elongate shaft 20. Accordingly, the surgical stapler 10 can be configured such that the handle assembly 40 can be reused with multiple shaft assemblies and reload cartridges during a surgical procedure. It is contemplated that in other embodiments, the handle assembly and some portion of the elongate shaft can be reusable while a remainder of the elongate shaft and the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reusable.

Figure 4:
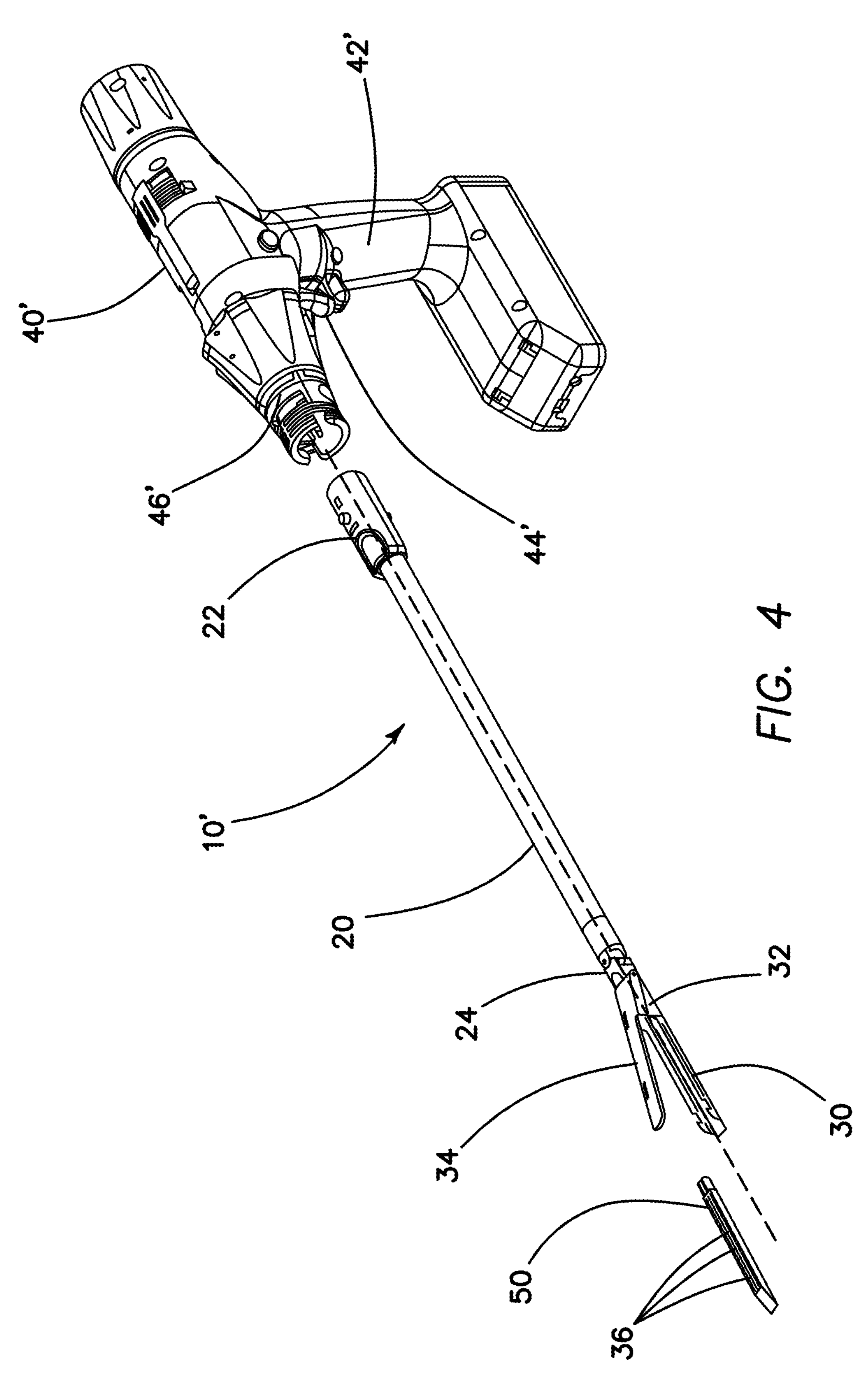
FIG. 4 is a perspective view of an embodiment of surgical stapling system having an embodiment of powered handle.
Figure 5:
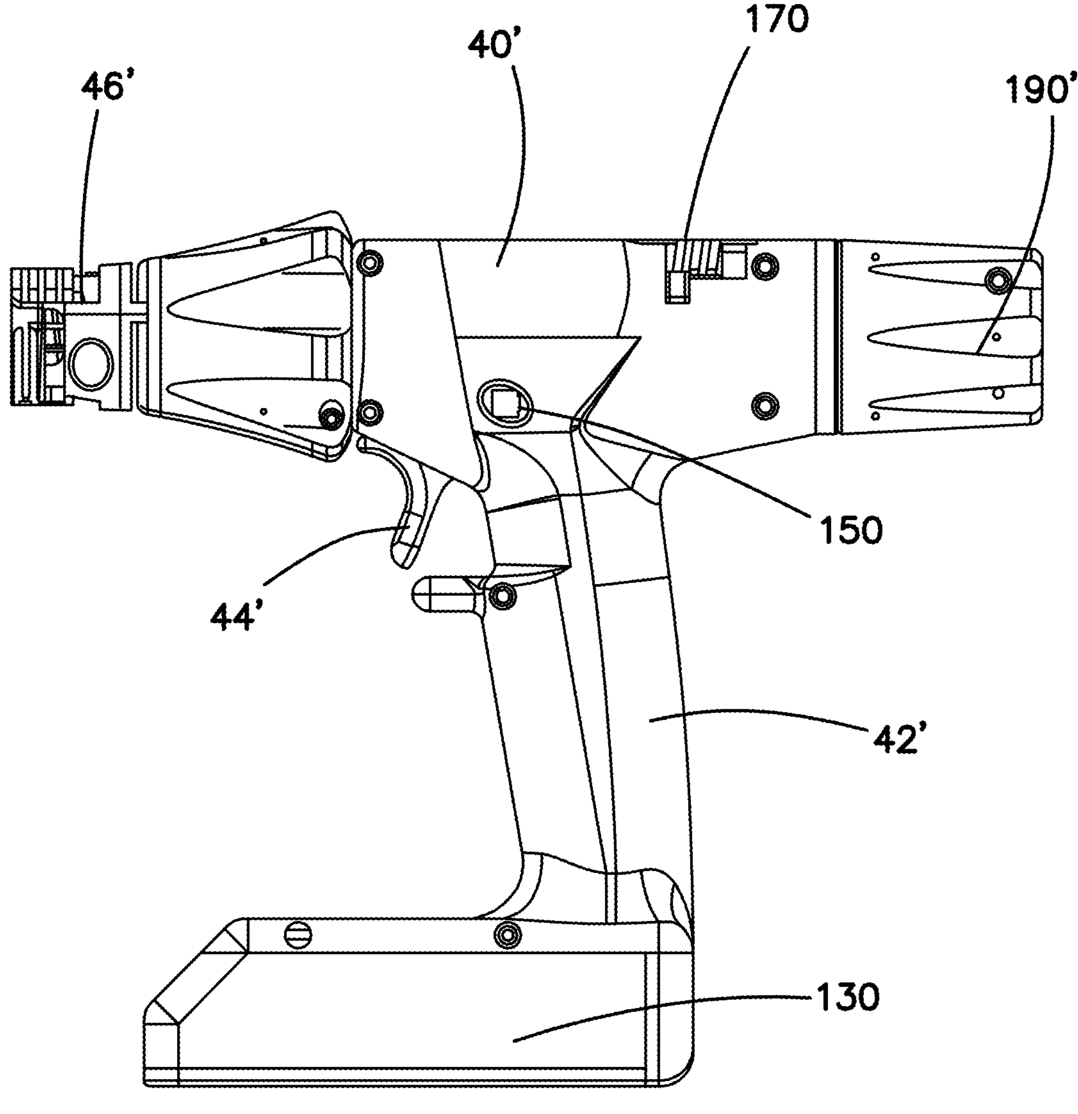
FIG. 5 is a side view the powered handle of the surgical stapling system of FIG. 1.
Figure 6:
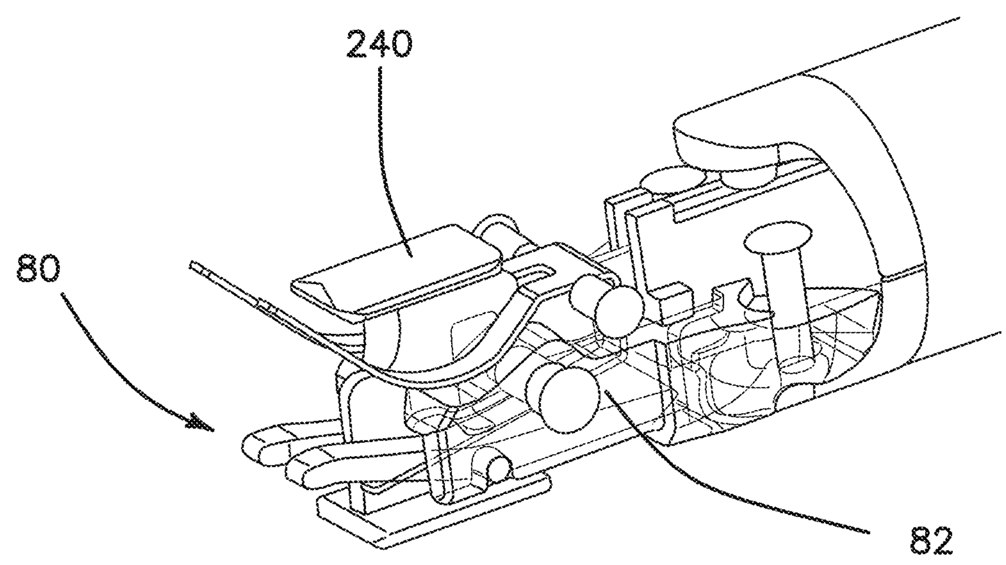
FIG. 6 is a perspective view of a reload lockout mechanism of the shaft assembly.
Figure 7:
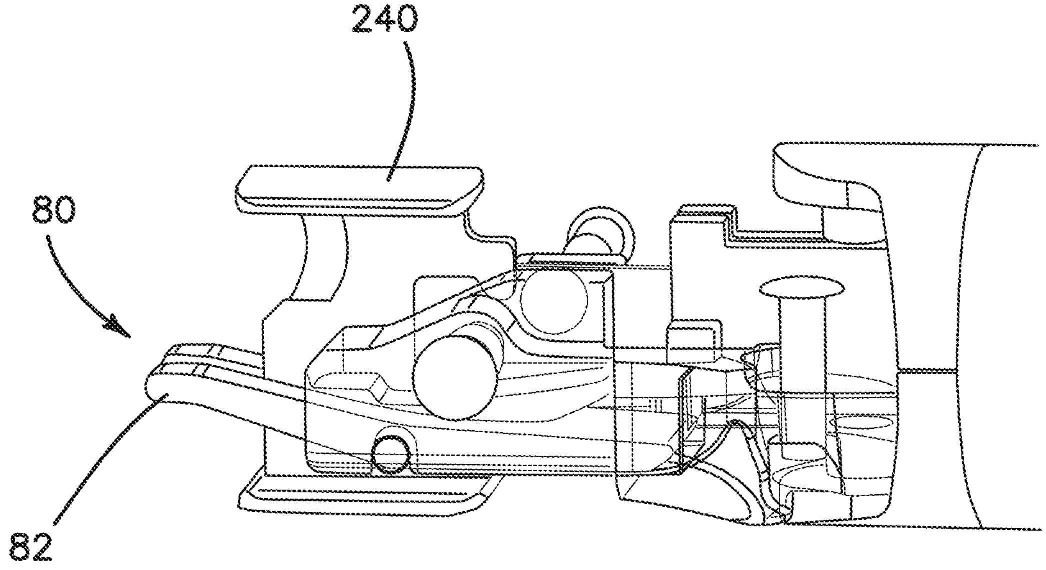
FIG. 7 is a side view of the reload lockout mechanism of the shaft assembly.

With reference to FIGS. 4-5, an embodiment of surgical stapling system with a powered handle assembly is illustrated. The illustrated embodiment of surgical stapler 10' comprises an elongate shaft 20, a jaw assembly 30, and a handle assembly 40'. FIG. 4 illustrates the surgical stapler 10' with the jaw assembly 30 in an open configuration with an embodiment of powered handle having powered staple firing and manual jaw assembly articulation. FIG. 5 illustrates the powered handle 40' of the surgical stapler system 10' with the elongate shaft removed. In the illustrated embodiments, the shaft 20 and jaw assembly 30 can be freely rotated about a longitudinal axis defined by the shaft 20 by rotation of a rotation knob on the handle 40'. In other embodiments, the stapling system can be configured to allow rotation of the jaw assembly about the longitudinal axis within a predefined range or a rotationally fixed jaw assembly.

With reference to FIG. 5, an embodiment of powered handle for a surgical stapling system is illustrated. The powered handle can be used with various shaft reloads and cartridges such that the shaft configuration, jaw assembly configuration, and staple configuration can be selected for a particular procedure. The motor is controlled by an embedded control system that dictates functionality of the handle during different stages of use. Articulation of the jaw assembly can be manually controlled by an articulation knob 190' that the operator rotates. In the illustrated embodiment, the articulation knob 190' is positioned on the proximal end of the powered handle and is rotatable about an axis generally corresponding to the longitudinal axis of the stapling system.

With continued reference to FIG. 5, the powered handle 40' comprises a pistol-grip configuration with a stationary handle 42' and a movable handle 44' or trigger pivotably coupled thereto. A power supply 130 or battery can be positioned on a lower surface of the stationary handle. The powered handle 40' can further comprise a user control such as a fire or fire/reverse button 150 to allow a user to selectively control a stapling sequence such that a user can selectively actuate the handle assembly to operate a jaw assembly in an open-close stroke and a firing stroke. The powered handle 40' can further comprise a redundant, manual override return system 170 to allow a user to manually return the stapling system to an open configuration in the event of a powered system failure, control system failure, power supply failure, "lockjaw," or other mechanical binding.

Various embodiments of powered handle assemblies and associated actuation mechanisms are disclosed in U.S. patent application Ser. No. 15/486,227, filed Apr. 12, 2017, entitled "Reload Shaft Assembly for Surgical Stapler" and U.S. patent application Ser. No. 15/486,008, filed Apr. 12, 2017, entitled "Surgical Stapler Having a Powered Handle," both of which are incorporated by reference herein in their entireties.

Figures 8, 9:
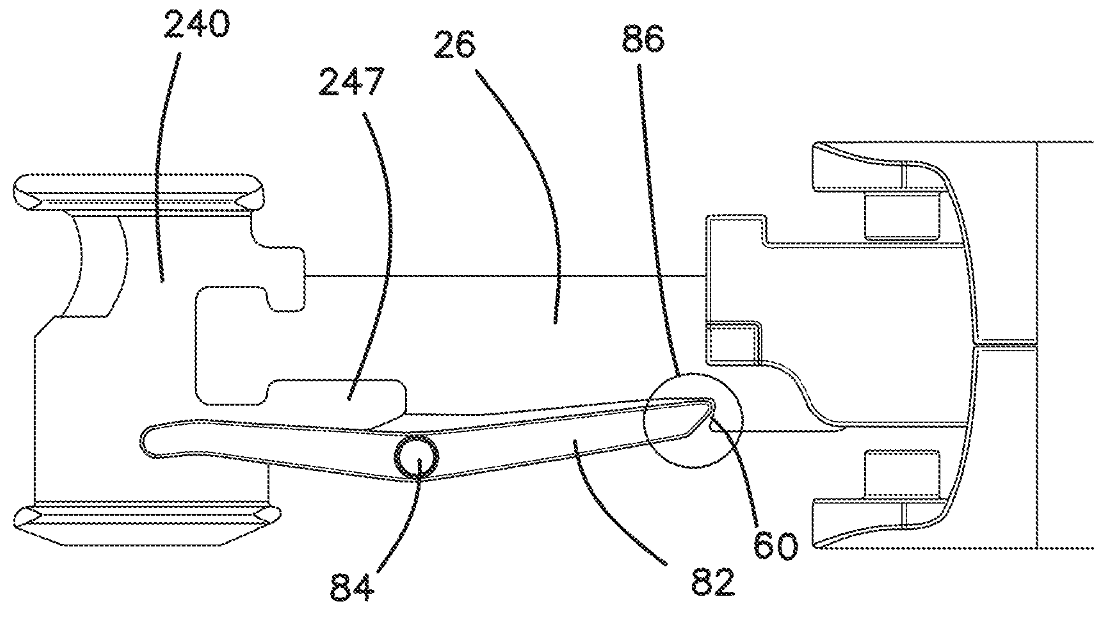
FIG. 8 is a side view of the reload lockout mechanism of the shaft assembly in a locked configuration.
FIG. 9 is a side view of the reload lockout mechanism of the shaft assembly in an unlocked configuration.

With reference to FIGS. 6, 7, 8, and 9, in certain embodiments, the jaw assembly can comprise a binary reload lockout mechanism 80. The reload lockout mechanism 80 can prevent advancement of the firing member if no reload is positioned within the jaw assembly or if an empty reload is positioned within the jaw assembly. The reload lockout mechanism 80 includes a lockout lever 82 pivotally coupled to the reload support. An axis defined by the pivot extends generally transverse to the longitudinal axis of the elongate shaft. With the firing member 240 fully retracted such that the jaw assembly is in an open configuration, a tail 247 extending proximally from the firing member 240 maintains the lockout lever 82 pivoted to the unlocked position. In the illustrated embodiment, a proximal portion of the lockout lever 82 proximal the pivot is forked or bifurcated to receive the firing member 240 therein such that the tail 247 can act on a surface of the lockout lever 82 proximal the pivot. If no reload is inserted, an attempt to advance the firing member 240 will allow the lockout lever to pivot about a pivot point 84 from the unlocked position to the locked position as the tail 247 of the firing member is advanced distally along the lockout lever. (FIG. 8). With the lockout lever 82 in the locked position, a proximal, locking end 86 of the lockout lever interferes with a lock recess 60 on the drive member 26, preventing further distal movement of the drive member.

With continued reference to FIGS. 6, 7, 8, and 9, if an unfired reload is inserted into the reload support (FIG. 9), a tail 54 extending proximally from a slider 55 engages a distal end of the lockout lever 82. The slider 55 is longitudinally distally slidable within the reload from a proximal position to a distal position to deploy a plurality of staples from the reload. As illustrated, the tail 54 acts on a lower surface of a distal portion of the lockout lever 82 distal the pivot point. This engagement of the slider tail 54 with the distal end of the lockout lever 82 pivots the proximal end of the lookout lever 82 away from the drive member 26 even once the tail 247 of the firing member 240 is no longer acting on the proximal portion of the lockout lever. Accordingly, the drive member 26 and firing member 240 can be distally advanced to fire the staples from the reload. Upon completion of a firing stroke, the slider 55 remains at a distal end of the reload. Thus if the jaw assembly is returned to the open configuration, withdrawing the firing member, the fired reload should be removed and a new unfired reload should be inserted to unlock the reload lockout.

While the binary lockout lever reload lockout mechanism described with respect to FIGS. 6-9 advantageously prevents firing of the jaw assembly when either no reload cartridge is present or a partially or fully fired reload is present, in certain conditions, it can allow a user to operate the handle assembly to actuate the jaw assembly in an open-close operation and an initial portion of the firing stroke, which can close the jaw assembly, and advance the firing member 240 to a pre-fired position in the jaw assembly. Safety of the binary lockout mechanism can be enhanced by positioning the lock recess 60 of the drive member in a location corresponding to a position on the firing member 240 within the open-close stroke of the jaw assembly such that with the lockout mechanism in a latched state the blade of the firing member 240 is recessed or through inclusion of a stop or guard member to shield the blade of the firing member. But, further improvements and advantages can be achieved with a separate empty jaw assembly lockout mechanism and fired reload lockout mechanism. As further described below, in certain embodiments, these separate mechanisms can be engaged by a two-position lockout lever, with two lockout positions and one unlocked position (FIGS. 12-19) or a lockout lever assembly having two independently-operable lockout levers (FIGS. 21-27).

Figures 10, 11:
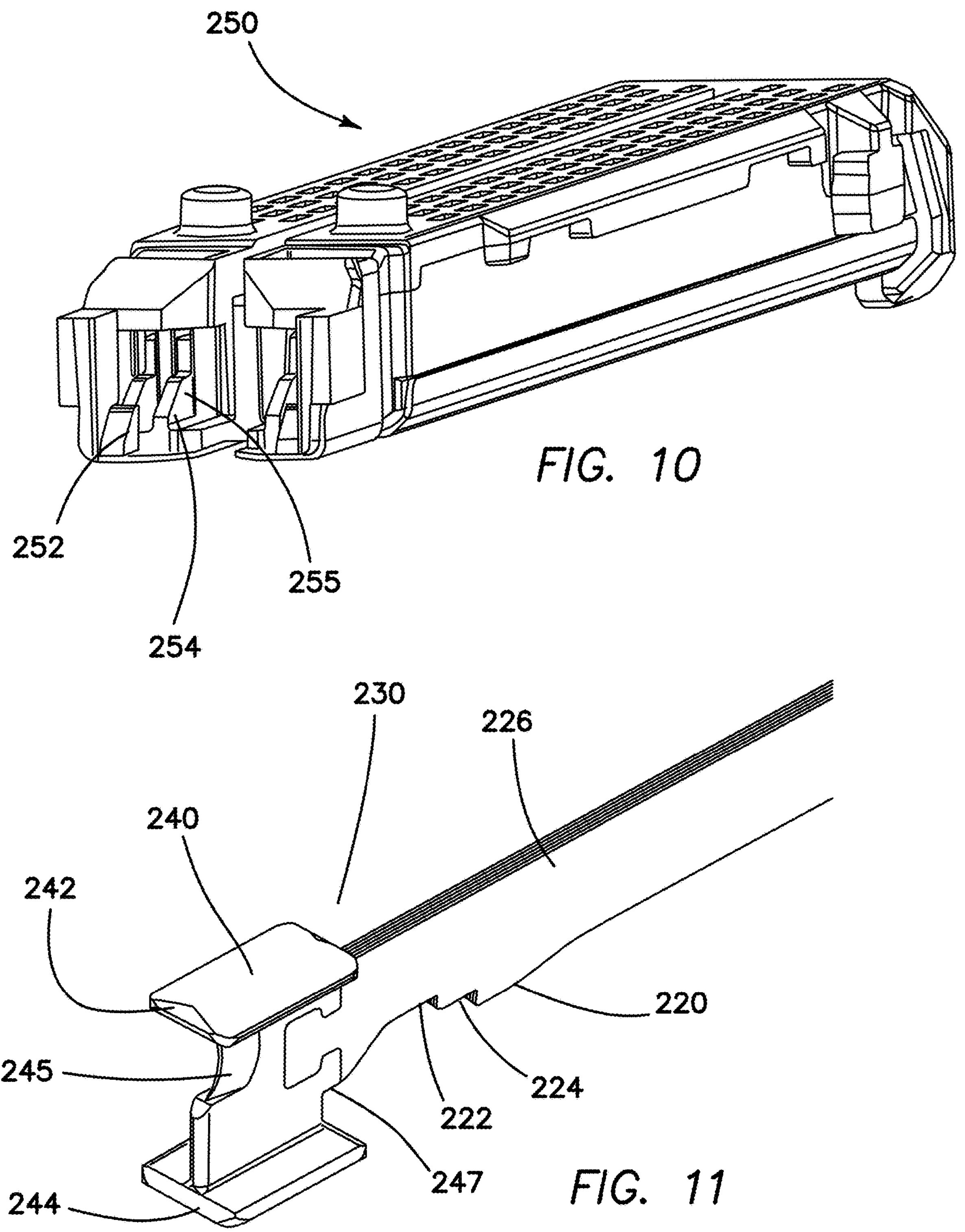
FIG. 10 is a perspective view of a reload cartridge for use in certain embodiments of surgical stapling device.
FIG. 11 is a perspective view of a firing beam and firing member for use in certain embodiments of elongate shaft assembly of a surgical stapling device.

With reference to FIG. 10, a reload cartridge 250 for use with an elongate shaft of a surgical stapler device having separate empty jaw assembly and fired reload lockout mechanisms is illustrated. As further described below, if no reload cartridge 250 is present in the jaw assembly and a user attempts to grasp the jaw assembly in an open-close stroke, a two-position lockout lever will move to a first, locked position. As illustrated, the reload cartridge includes a first lockout actuator sized and positioned to position a two-position lockout lever in a second position to defeat the empty jaw assembly lockout mechanism when a reload is positioned in the reload support of the jaw assembly. In certain embodiments, the first lockout actuator can comprise a ramped boss 252 extending laterally inwardly from a side wall of a body of the cartridge.

With continued reference to FIG. 10, in the illustrated embodiment the reload cartridge 250 includes a second lockout actuator sized and configured to position a two-position lockout lever in an unlocked position to defeat the fired reload lockout mechanism when an unfired reload is positioned in the jaw assembly. Thus, in addition to the two lockout positions, the two-position lockout lever is pivotable to an unlocked position. In certain embodiments, the second lockout actuator comprises a tail 254 extending proximally from a slider 255 of the reload cartridge 250. When the reload cartridge 250 is in an unfired state, the slider 255 is in a proximal position such that the slider tail 254 extends proximally to engage the lockout lever. As the firing member is advanced distally in a firing stroke, it abuts the slider within the reload cartridge and advances the slider distally. Advancement of the slider 255 longitudinally distally within the reload from the proximal position to a distal position deploys a plurality of staples from the reload. Thus, once the reload cartridge 250 is in a partially fired (or fully fired) state, the proximally-extending slider tail 254 is not in position to defeat the fired reload lockout mechanism.

With reference to FIG. 11, a firing beam 226 for use with an elongate shaft assembly of a surgical stapler device having separate empty jaw assembly and fired reload lockout mechanisms is illustrated. The firing beam 226 extends from a proximal end to a distal end 230. A firing member 240 having a generally I-beam configuration is disposed at the distal end 230 of the firing beam 226. Upper and lower horizontal flanges 242, 244 of the I-beam firing member 240 ride in channels in the first and second jaws of the jaw assembly to approximate the jaws, then maintain spacing of the jaws during staple firing. A cutting blade 245 is positioned on the vertical portion of the I-beam profile to transect tissue between rows of staples. The I-beam firing member 240 can be attached to the distal end of the firing beam 226 by an interlock fit, welding, another joining technique, or some combination thereof. A proximal edge of the I-beam firing member 240 can have a proximally-extending projection or tail 247 that can rest on a proximal portion of a lockout lever with the firing beam 226 in a fully retracted position corresponding to an open jaw assembly.

With continued reference to FIG. 11, the firing beam can include a first lockout notch 222 for use in conjunction with the empty jaw assembly lockout mechanism and a second lockout notch 224 for use in conjunction with the fired reload lockout mechanism. In the illustrated embodiment, the first lockout notch 222 extends a first height from an adjacent lower edge 220 of the firing beam 226. As further described below, the first height is selected to correspond to a height of the proximal end of the lockout lever when the empty jaw assembly lockout has been actuated by an attempt to approximate a jaw assembly without a reload cartridge present.

With continued reference to FIG. 11, in the illustrated embodiment, the second lockout notch 224 is positioned on the firing beam proximal of the first lockout notch 222. The second lockout notch 224 extends a second height from the adjacent lower edge 220 of the firing beam 226. As further described below, the second height is selected to correspond to a height of the proximal end of the lockout lever when the fired reload lockout mechanism has been actuated by an attempt to fire a previously fired or partially fired reload.

The illustrated embodiment of firing beam 226 has a first lockout notch 222 and a second lockout notch 224 that are substantially contiguous such that the adjacent lower edge 220 of the firing beam is relieved over a longitudinal span corresponding to the first lockout notch 222 and the second lockout notch 224. It is contemplated that in other embodiments, the first lockout notch and the second lockout notch can be spaced from one another by an unrelieved segment of the lower edge of the firing beam. As further described herein, the heights and longitudinal positions of the first lockout notch and the second lockout notch can be configured to achieve desired operational characteristics of a stapler handle assembly.

Figure 12:
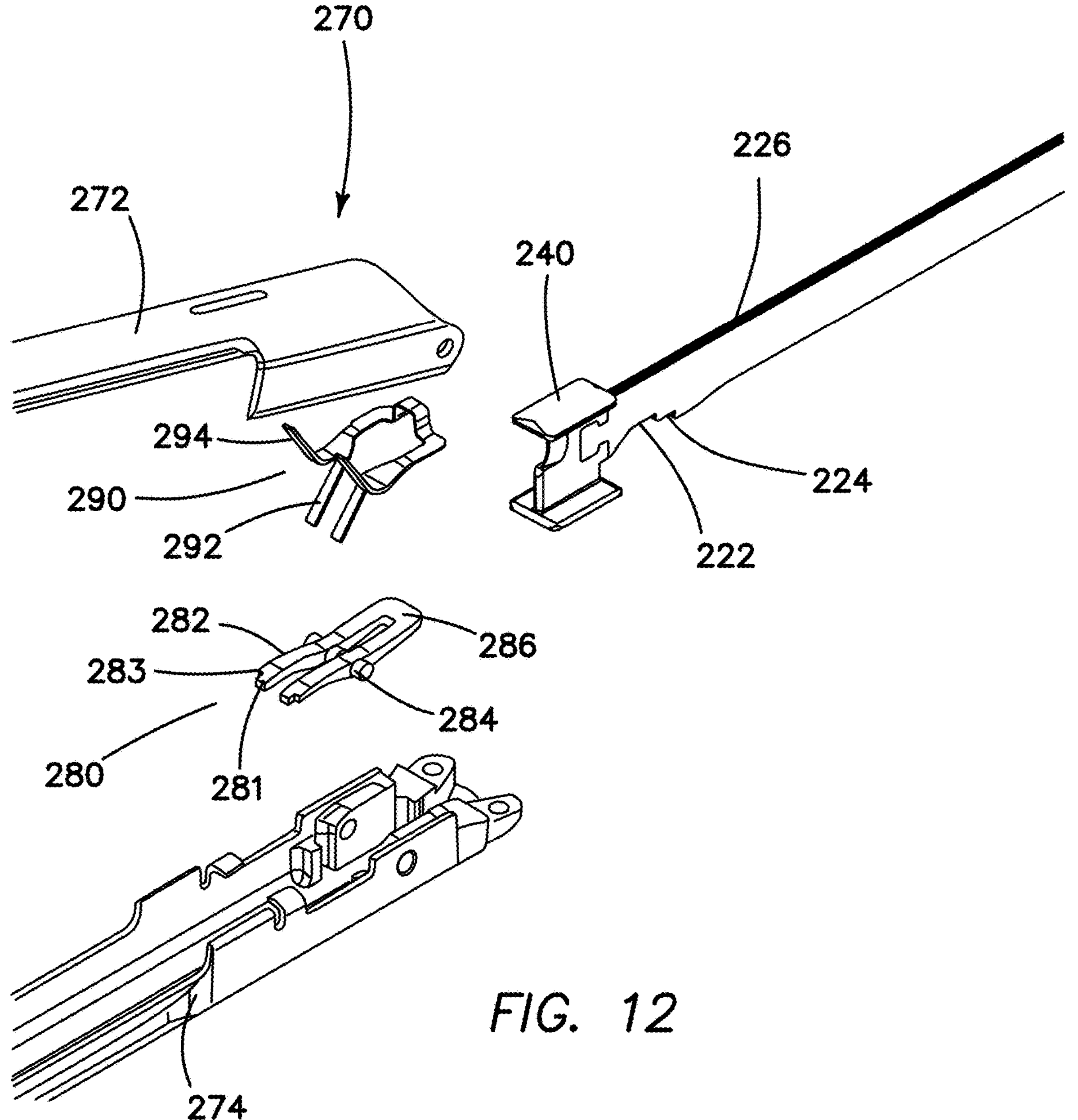
FIG. 12 is a partially exploded perspective view of a proximal end of a jaw assembly of certain embodiments of elongate shaft assembly of a surgical stapling device.
Figure 13:
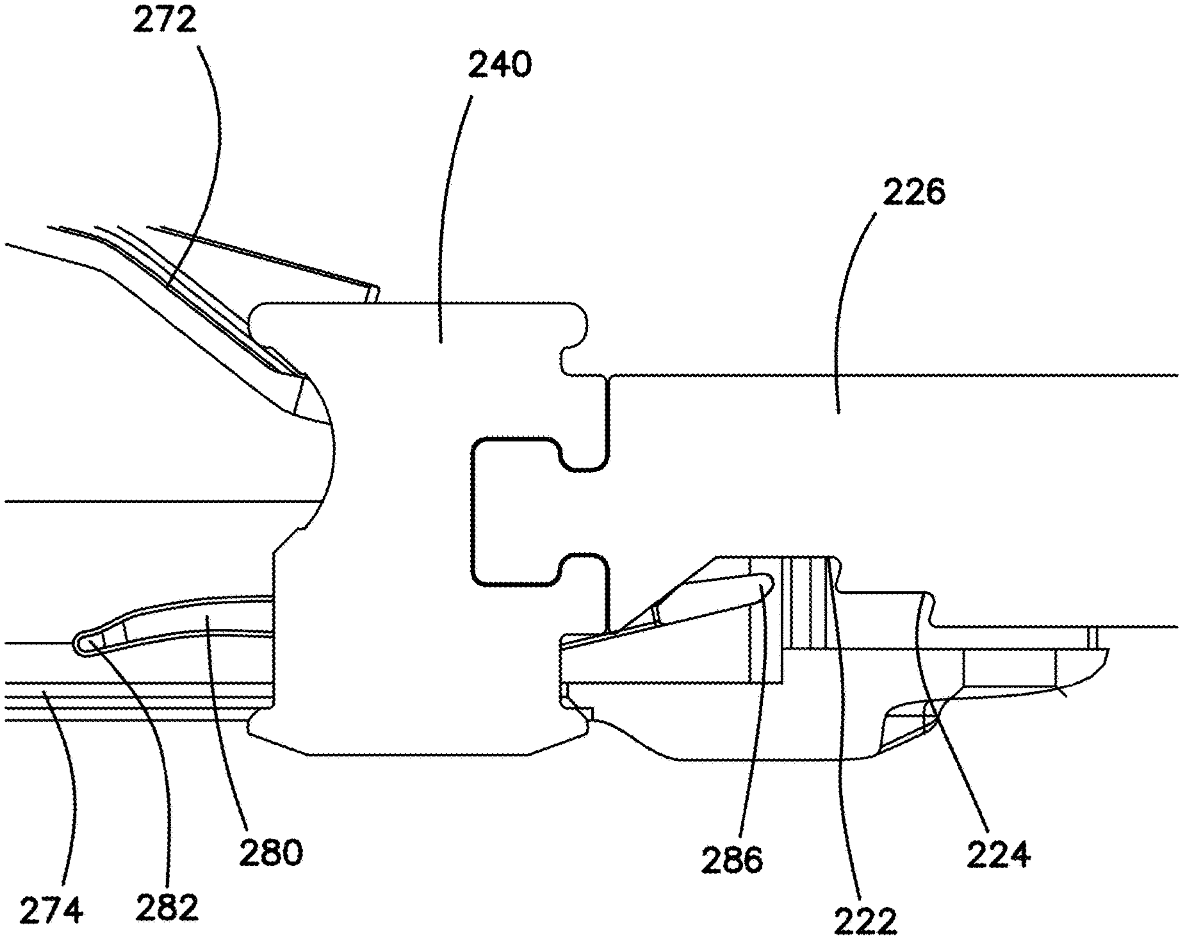
FIG. 13 is a cut away side view of a proximal end of a jaw assembly of certain embodiments of elongate shaft assembly of a surgical stapling device.

With reference to FIGS. 12 and 13, a portion of the jaw assembly 270 is illustrated in partially exploded (FIG. 12) and cut away side views (FIG. 13), with various components hidden for illustration of the empty jaw assembly lockout mechanism and the fired reload lockout mechanism. In certain embodiments, the lockout mechanisms comprise a two-position lockout lever 280, a biasing spring 290, a first lockout notch 222, and a second lockout notch 224. The two-position lockout lever 280 has a distal end 282 configured to engage a first lockout actuator and a second lockout actuator on a reload cartridge, a pivot 284 proximal the distal end, and a proximal end 286 configured to engage either the first lockout notch, the second lockout notch, or neither. The biasing spring 290 has at least one lower spring arm 292 biasing the end of the lockout lever 280 distal the pivot 284 in a downward direction towards the reload support of the second jaw 274. In the illustrated embodiment, the biasing spring has two lower spring arms 292 with a gap therebetween allowing passage of the firing member 240 and the firing beam 226. The biasing spring 290 can have at least one upper spring arm 294 that biases the first jaw 272 towards an open configuration. The biasing spring 290 can be configured to sit astride the firing beam 226 and can have a central saddle member from which the at least one lower spring arm 292 and the at least one upper spring arm 294 extend.

Figure 16:
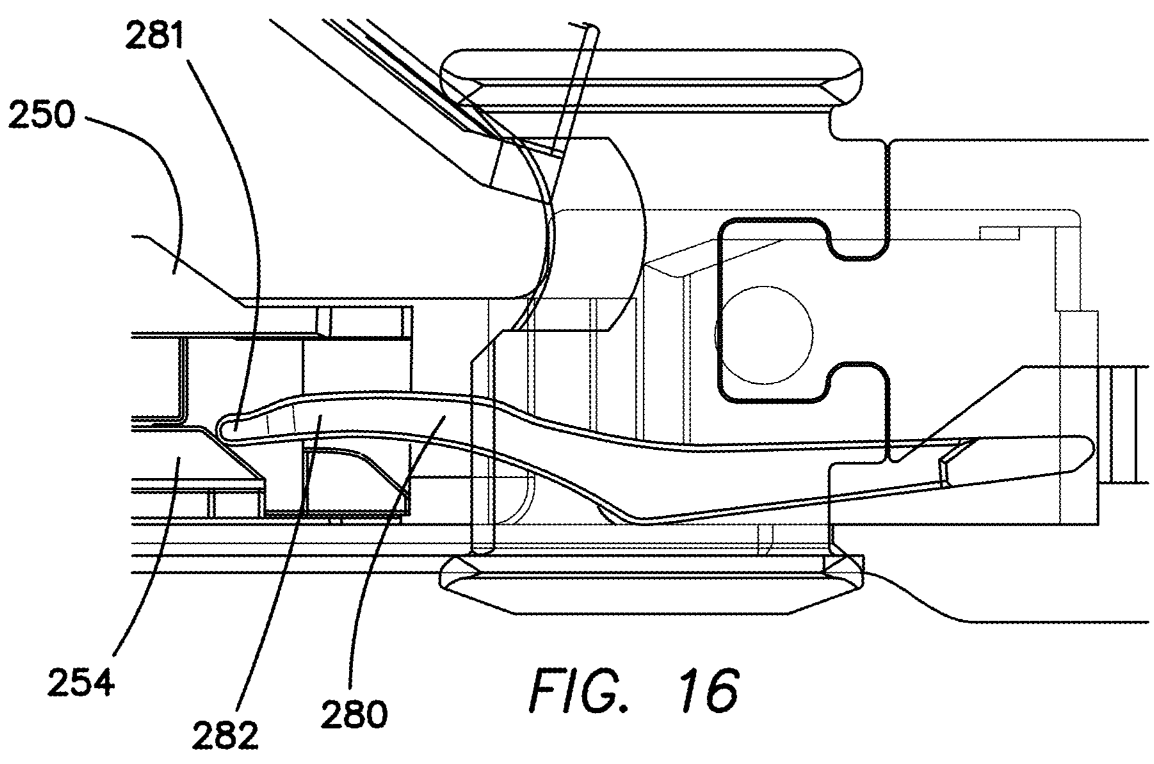
FIG. 16 is a cut away side view of the proximal end of the jaw assembly of FIG. 13 with an unfired reload partially inserted.
Figure 17:
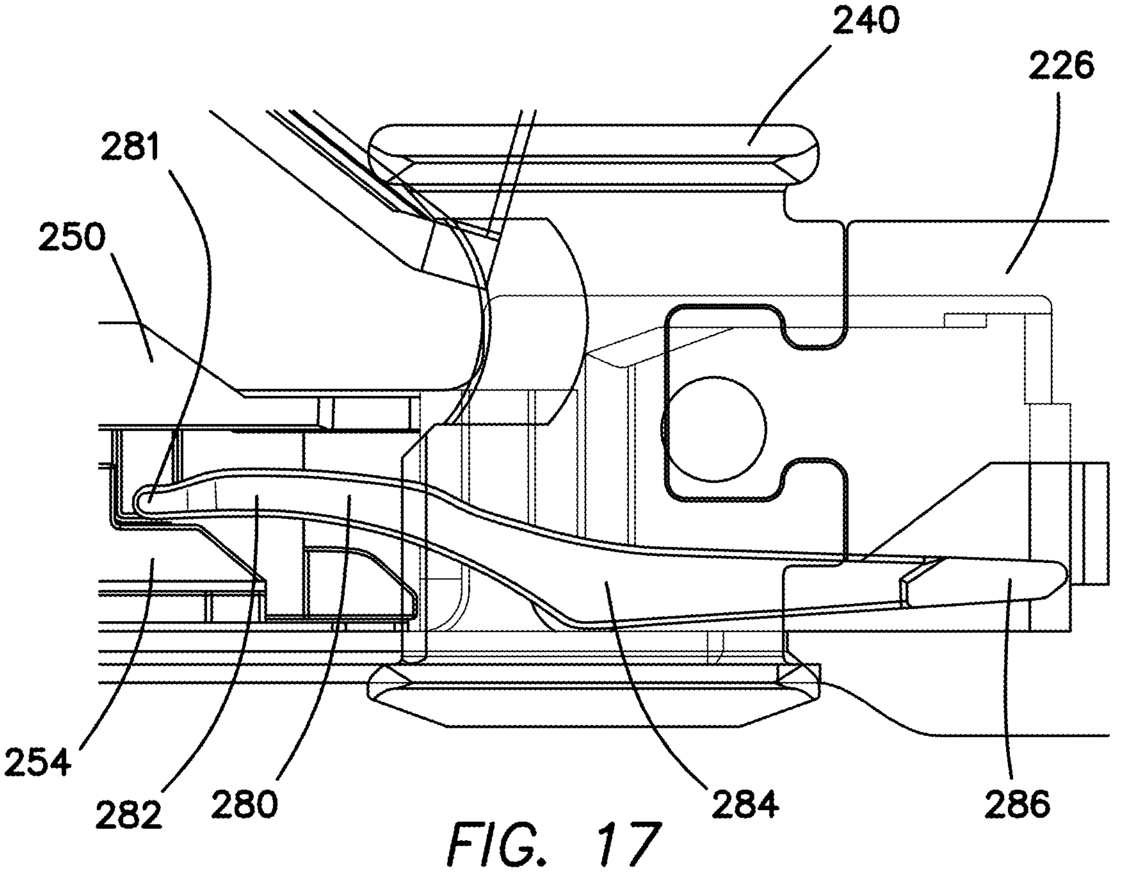
FIG. 17 is a cut away side view of the proximal end of the jaw assembly of FIG. 13 with an unfired reload inserted.
Figure 18:
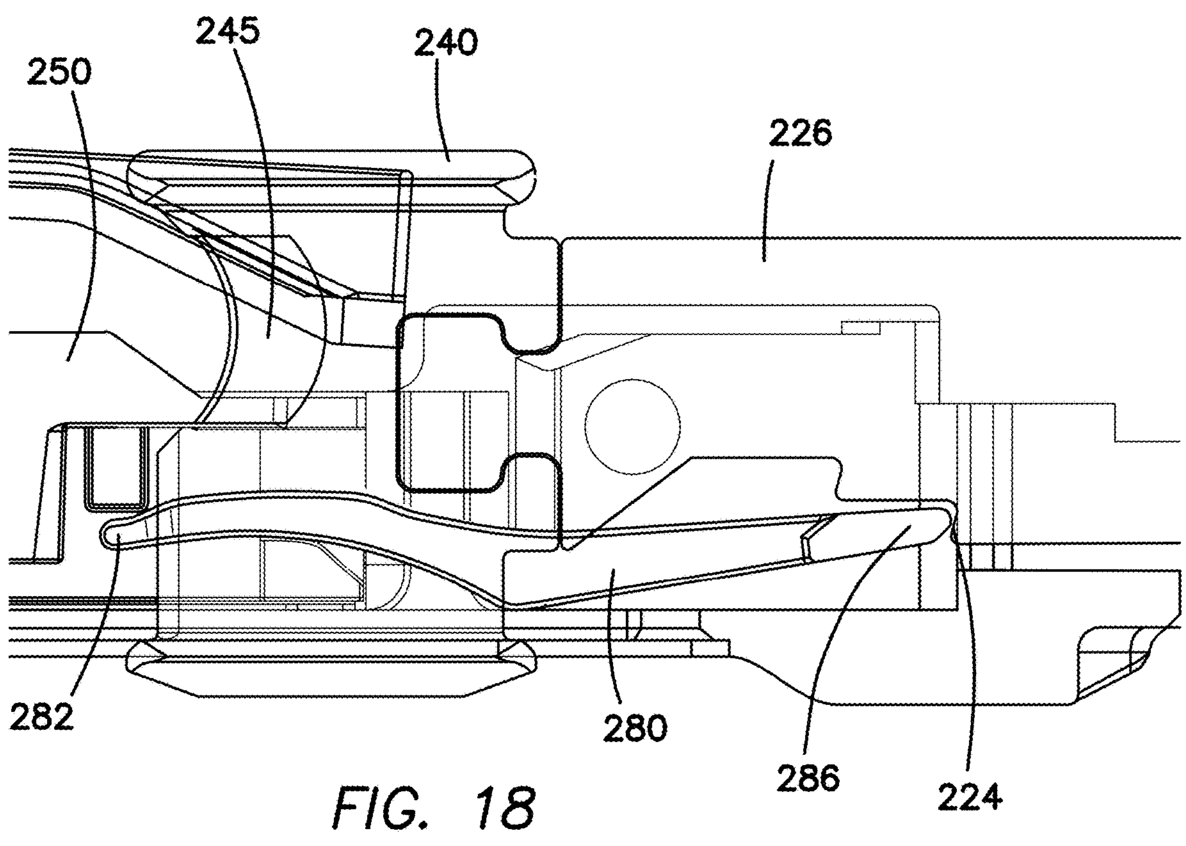
FIG. 18 is a cut away side view of the proximal end of the jaw assembly of FIG. 13 with an at least partially fired reload inserted.
Figure 19:
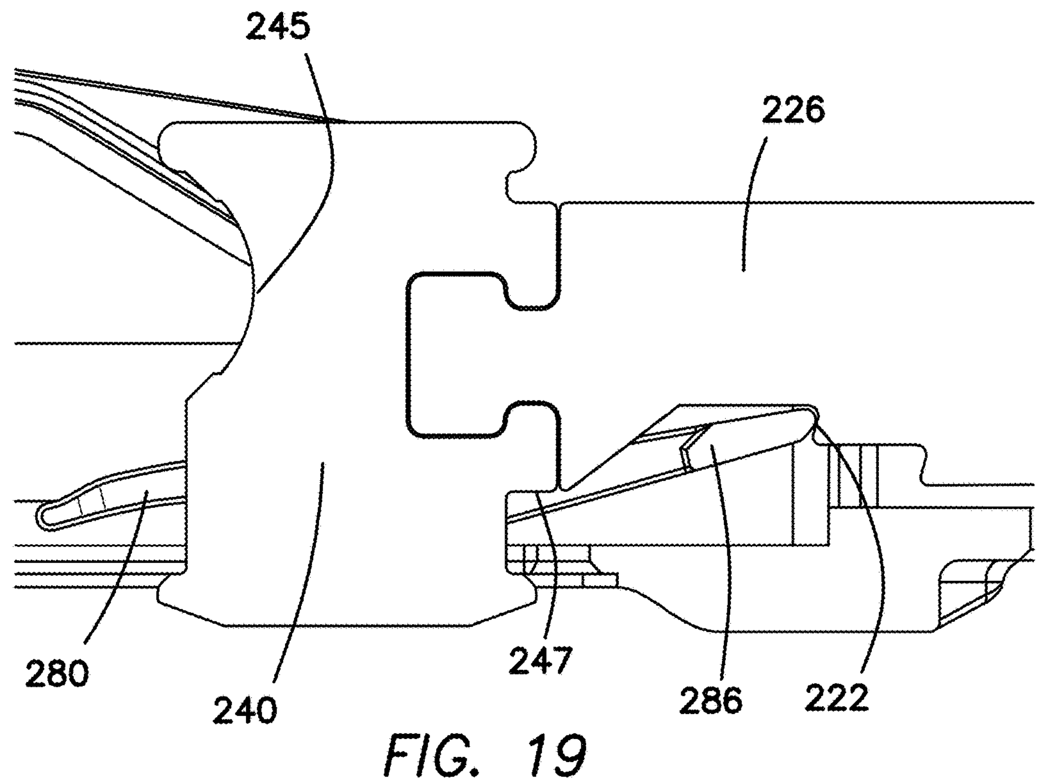
FIG. 19 is a cut away side view of the proximal end of the jaw assembly of FIG. 13 with no reload inserted.

With reference to FIGS. 14-19, operation of the two lockout mechanisms is illustrated. In these partial cut away side views of a proximal end of certain embodiments of jaw assembly, certain elements of the jaw assembly (such as biasing spring) are not illustrated, and certain components (such as firing member 240) are illustrated as transparent elements to enhance visibility of the operation of the lockout mechanisms. FIGS. 14-17 illustrate functioning of the lockout mechanisms as a full, unfired staple reload 250 cartridge is positioned in the reload support of the second jaw 274. FIG. 18 illustrates operation of the fired reload lockout mechanism. FIG. 19 illustrates operation of the empty jaw assembly lockout mechanism.

Figure 14:
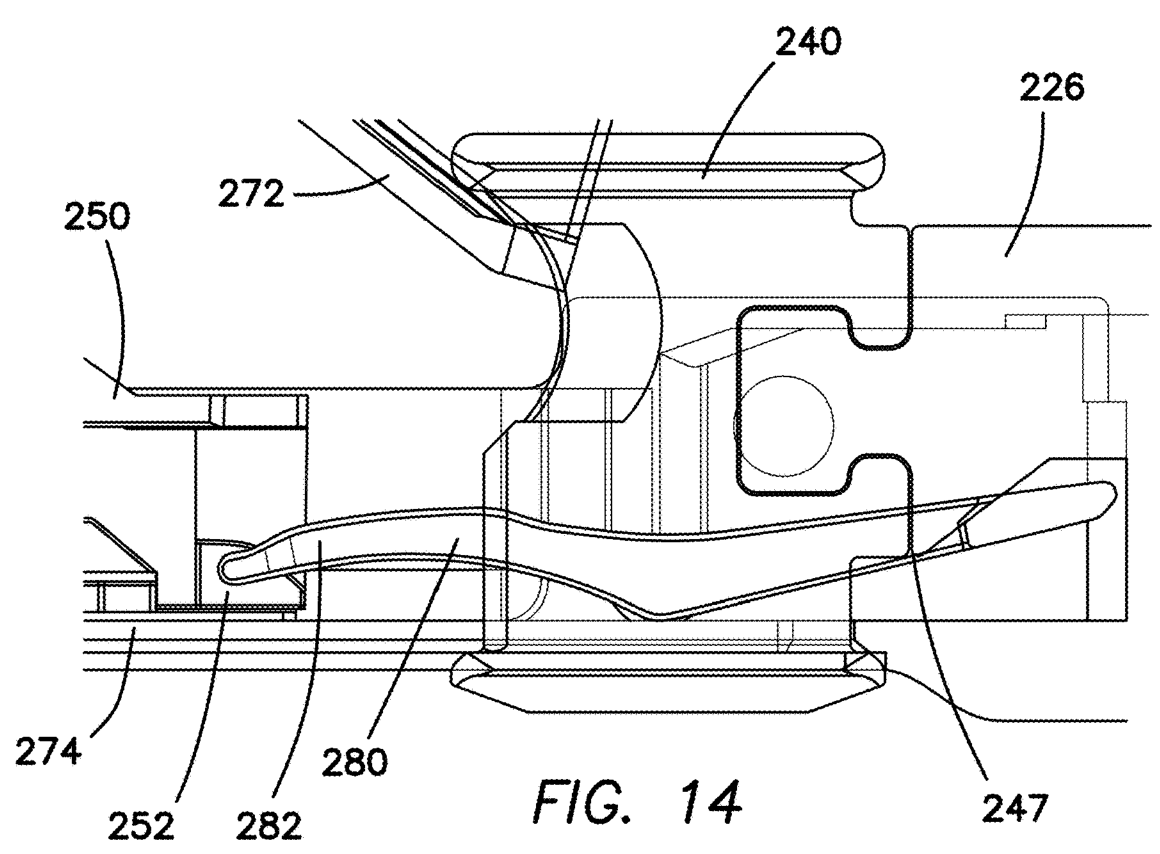
FIG. 14 is a cut away side view of the proximal end of the jaw assembly of FIG. 13 with an unfired reload partially inserted.

With reference to FIG. 14, a cut away view of the proximal end of the jaw assembly is illustrated. The jaw assembly is in an open configuration such that the first jaw 272 is biased to an open position relative to the second jaw 274. The firing member 240 and firing beam 226 are in a fully proximally retracted position such that a proximal surface of the lockout lever 280 rests on a proximally extending tail 247 of the firing member 240. Thus, the distal end 282 of the lockout lever 280 is raised slightly away from the reload support such that a lockout actuator can be positioned between the reload support and the lockout lever 280.

With continued reference to FIG. 14, the slight raise of the distal end 282 of the lockout lever 280 can accept a ramped proximal surface of the first lockout actuator or ramped boss 252 formed on the reload cartridge body. The distal end 282 of the lockout lever 280 has a lateral extension 283 (FIG. 12) positioned to engage the first lockout actuator and a medial surface 281 (FIG. 12) positioned to engage the second lockout actuator as the reload cartridge 250 is slid proximally upon insertion to the reload support of the jaw assembly.

Figure 15:
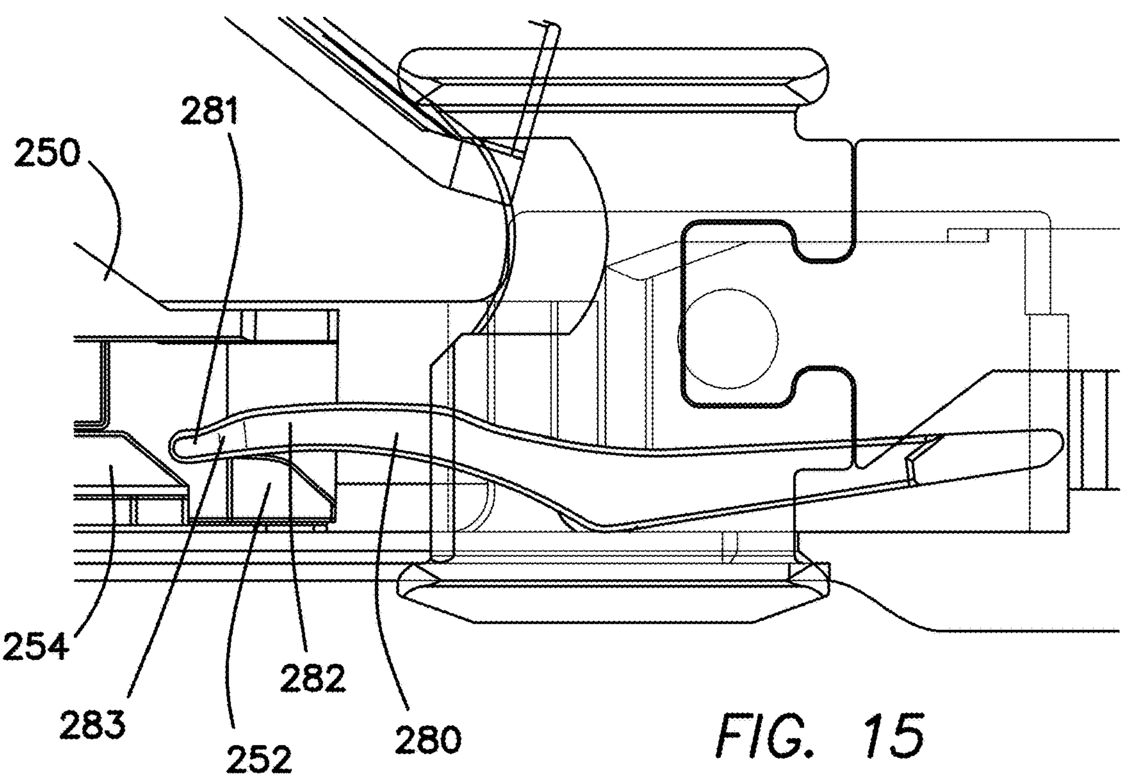
FIG. 15 is a cut away side view of the proximal end of the jaw assembly of FIG. 13 with an unfired reload partially inserted.

With reference to FIG. 15, a cut away view of the proximal end of the jaw assembly is illustrated with the reload 250 cartridge partially inserted. As illustrated, the lateral extension 283 of the distal end 282 of the lockout lever 280 has engaged a ramped proximal surface 283 of the ramped boss 252. As the reload 250 cartridge is further slid proximally, the lateral extension 283 travels up the ramped surface to a first height relative to the reload support, pivoting the lockout lever 280 into the second position and defeating the empty jaw assembly lockout mechanism. Operation of the empty jaw assembly lockout mechanism is further described below with reference to FIG. 19. In the illustrated embodiment, the second lockout actuator or slider tail 254 of an unfired reload 250 cartridge is positioned just distal of the first lockout actuator at a height positioned to engage with the medial surface 281 of the distal end 282 of the lockout lever 280 once the distal end 282 of the lockout lever 280 has been raised to the first height from the reload support by the first lockout actuator. Accordingly, when viewed in a cut away side view, as illustrated in FIG. 15, the first lockout actuator and second lockout actuator define a progressive ramped profile arranged to elevate the distal end

282 of the lockout lever 280 to two predefined positions as a reload 250 cartridge is inserted into the reload support.

With reference to FIG. 16, a cut away view of the proximal end of the jaw assembly is illustrated with the reload 250 cartridge almost fully inserted. As illustrated, the medial surface 281 on the distal end 282 of the lockout lever 280 has engaged a ramped proximal surface of the second lockout actuator or slider tail 254. In the illustrated embodiment, the proximally extending tail 254 of the slider of the reload 250 has a lead-in ramped surface that, with the reload cartridge in an unfired state, engages the distal end 282 of the lockout lever 280. In certain embodiments, the lockout lever 280 and slider tail 254 can be configured to provide a smooth, relatively low friction reload insertion and reduce the possibility of binding or inadvertent advancement of the slider during insertion of the cartridge. For example, in certain embodiments, the medial surface 281 of the distal end 282 of the lockout lever 280 can have a radiused distal tip such that the lockout lever 280 will be pivoted by interaction with the slider tail despite potential slight angular misalignments between the reload 250 cartridge and the reload support. Moreover, in certain embodiments, the ramped proximal surface of the slider tail 254 can extend from a first height relative to the reload support at a proximal end that is smaller than a height of the first lockout actuator relative to the reload support. Accordingly, as an unfired reload 250 cartridge is positioned in the reload support, the distal end 282 of the lockout lever 280 can transition from the first lockout actuator to the second lockout actuator smoothly at a wide range of angular alignments between the reload cartridge and reload support.

With reference to FIG. 17, a cut away view of the proximal end of the jaw assembly is illustrated with the reload 250 cartridge fully inserted. As illustrated, the medial surface 281 on the distal end 282 of the lockout lever 280 has been advanced along the ramped proximal surface of the second lockout actuator and onto the second lockout actuator or slider tail 254. This advancement along the ramped surface of the slider tail 254 pivots the lockout lever 280 about the pivot 284 such that the distal end 282 of the lockout lever 280 is at a second height with respect to the reload support. With the distal end of the lockout lever 280 at the second height, the lockout lever is in an unlocked position, corresponding to an unlocked state of the empty jaw assembly lockout mechanism and an unlocked state of the fired reload lockout mechanism.

With continued reference to FIG. 17, with the lockout lever 280 in the unlocked position, the proximal end 286 of the lockout lever 280 is positioned at a height below a lower edge of the firing beam. Accordingly, the firing member 240 and firing beam 226 can be distally advanced through an open-close stroke and a firing stroke responsive to user input from an operatively coupled mechanical or powered handle assembly (FIGS. 1-5). Accordingly, when an unfired reload cartridge is inserted to the reload support of the jaw assembly, both the empty jaw assembly lockout mechanism and the fired reload lockout mechanism are defeated to allow a user to operate a stapler handle assembly to grasp tissue with the jaw assembly and fire staples from the jaw assembly by distal translation of the firing beam and firing member within the jaw assembly.

With reference to FIG. 18, once a reload 250 cartridge has been at least partially fired, the slider within the reload 250 is advanced distally from a proximal, unfired position. Upon completion of a firing stroke, the slider remains at a distal location within the reload cartridge while the firing beam 226 and firing member 240 can be retracted proximally responsive to operation of a handle assembly in a return or retraction stroke. Thus, once a reload 250 cartridge has been partially or fully fired the second lockout actuator or slider tail is not in position to engage the distal end 282 of the lockout lever 280. In certain embodiments, the first lockout actuator or ramped boss 252, however, is stationary relative to a body of the cartridge. Thus, with a partially or fully fired reload 250 positioned in the reload support, the distal end 282 of the lockout lever 280 is engaged by the first lockout actuator to position the distal end 282 of the lockout lever 280 at the first height relative to the reload support. With the distal end 282 of the lockout lever 280 at the first height, corresponding to the second position of the lockout lever, the empty jaw assembly lockout mechanism is defeated, but the fired reload lockout mechanism is locked.

With continued reference to FIG. 18, with the lockout lever 280 in the second position, the proximal end 286 of the lockout lever 280 is at a height corresponding to the second lockout notch 224 on the firing beam 226. Moreover, in certain embodiments, the biasing spring 290 (FIG. 12) exerts a force on an upper surface of the distal end 282 of the lockout lever 280, tending to maintain the proximal end 286 of the lockout lever 280 at the height corresponding to the second lockout notch 224 on the firing beam 226. Accordingly, if a user attempts to actuate the jaw assembly with a fired reload cartridge present in the jaw assembly, the firing beam 226 can be distally advanced until the proximal end 286 of the lockout lever 280 seats within the second lockout notch 224 of the firing beam 226, indicating engagement of the fired reload lockout mechanism and preventing further distal motion of the firing beam and the firing member.

With continued reference to FIG. 18, in certain embodiments the fired reload lockout mechanism can be configured to permit operation of the jaw assembly of the stapling device in at least a portion of an open-close stroke. For example, in certain embodiments, the position of the second lockout notch 224 and the length of the lockout lever 280 can be sized and configured such that the firing beam 226 is arrested upon engagement of the fired reload mechanism at a position corresponding to a fully closed or almost fully closed configuration of the jaw assembly. With the jaw assembly in such a configuration, the firing member 240 has advanced to a distal position that approximates the first jaw and the second jaw, but maintains the cutting edge 245 in a substantially recessed location. Advantageously, with the fired reload lockout configured to permit an open-close stroke, after firing staples from a reload cartridge, a user can operate the jaw assembly in one or more open-close strokes to assess tissue thicknesses and consistency at various locations for application of a potential second reload. Likewise, as insertion of a stapling device through a surgical access port such as a trocar can typically require the jaw assembly to be in a closed configuration, a user could withdraw and reinsert the jaw assembly through one or more surgical access ports to evaluate tissue thicknesses and consistency at various locations in a surgical site.

With continued reference to FIG. 18, in certain embodiments, the fired reload lockout mechanism can be further configured to prevent operation of the stapling device in a firing stroke. Mechanical and powered stapler handle assemblies configured for use with an elongate shaft and jaw assembly as described herein, such as those discussed above with respect to FIGS. 1-5, typically include firing mode selector mechanisms or firing safety switches to allow a user to affirmatively select operation of a firing stroke of the jaw assembly only once the jaw assembly has been positioned in a closed configuration. Thus, in certain embodiments, the position of the second lockout notch 224 and the length of the lockout lever 280 can be sized and configured such that the firing beam is arrested upon engagement of the fired reload lockout mechanism at a position corresponding to a position proximal to a fully closed configuration of the jaw assembly. Thus, in these embodiments, once the fired reload lockout mechanism has been engaged, although a user would be able to select operation of the firing stroke on the handle assembly, the handle assembly would not engage the firing beam in a firing stroke. Advantageously, operation of the fired reload lockout mechanism to prevent actuation of the firing stroke on the handle assembly would serve as an indication to the user that a lockout had been engaged.

With reference to FIG. 19, a cut away view of the proximal end of the jaw assembly is illustrated with no reload cartridge inserted and the firing member and firing beam slightly longitudinally advanced. With no reload present, once the tail 247 of the firing member 240 advances off of the proximal end 286 of the lockout lever 280, the biasing spring 290 (FIG. 12) exerts force on the upper surface of the distal end 282 of the lockout lever 280 towards the reload support. Thus, upon initial advancement of the firing beam 226 responsive to a user actuating a handle assembly to advance the jaw assembly in an open-close stroke, the lockout lever 280 is pivoted into a first position corresponding to a locked configuration of the empty jaw assembly lockout mechanism. As the firing beam 226 is advanced distally, the proximal end 286 of the lockout lever 280 seats in the first lockout notch 222 on the firing beam 226 and engages the empty jaw assembly lockout mechanism, preventing further distal translation of the firing beam 226 and firing member 240.

With continued reference to FIG. 19, in certain embodiments the empty jaw assembly lockout mechanism can be configured to arrest motion of the firing beam at a position corresponding to a substantially open configuration of the jaw assembly. For example, the position of the first lockout notch 222 on the firing beam 226, the length of the lockout lever 280, and the length of the tail 247 of the firing member 240 can be sized and configured such that the empty reload lockout mechanism is locked early in an open-close stroke of the jaw assembly. Advantageously, with the empty jaw assembly lockout mechanism configured to lock during an initial portion of the open-close stroke, a user would be unable to actuate a handle assembly to close the jaw assembly sufficiently to be inserted through a surgical access port if no reload cartridge were present in the jaw assembly. Thus, with an empty jaw assembly lockout mechanism so configured, a user would have a tactile indication that no reload cartridge is present in the jaw assembly before inadvertently introducing an empty jaw assembly to a surgical site. Moreover, such an empty jaw assembly lockout desirably maintains the cutting edge 245 of the firing member 240 in a substantially retracted, shielded position relative to the jaw assembly with no reload present in the jaw assembly.

With reference to FIGS. 20-27, in certain embodiments, an elongate shaft and jaw assembly for use in a surgical stapling device can have independently-operable empty jaw assembly and fired reload lockout mechanisms. In the illustrated embodiment, rather than including a two-position lockout lever having surfaces actuatable by first and second lockout actuators, as described with reference to FIGS. 10-19, the jaw assembly can include a first lockout lever and a second lockout lever independently actuatable by corresponding first and second lockout actuators.

Figures 20, 21:
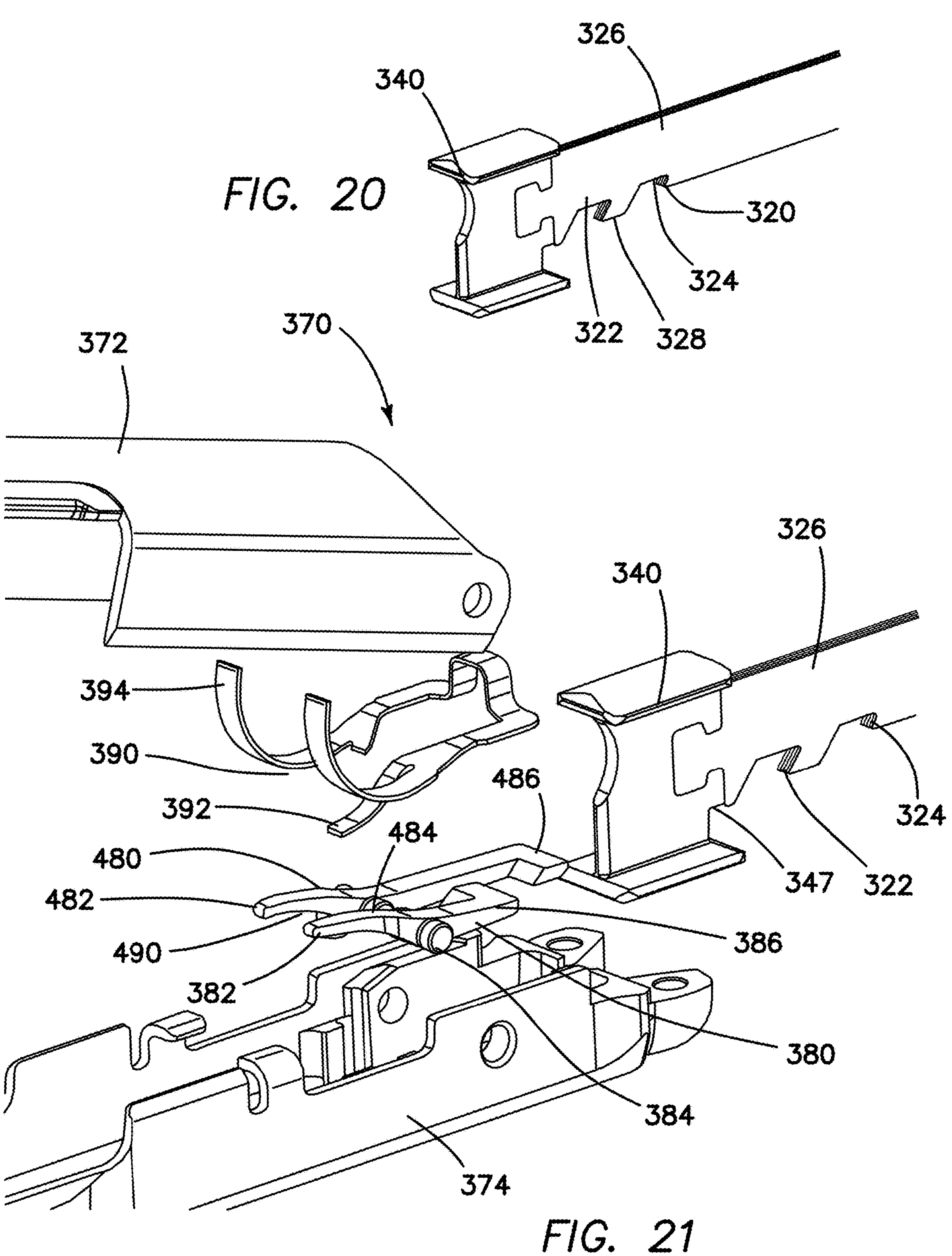
FIG. 20 is a perspective view of a firing beam and firing member for use in certain embodiments of elongate shaft assembly of a surgical stapling device.
FIG. 21 is a perspective partially exploded view of a proximal end of a jaw assembly for use in certain embodiments of elongate shaft assembly of a surgical stapling device.

With reference to FIG. 20, an embodiment of firing beam 326 for use with the lockout mechanisms of FIGS. 21-27 is illustrated. In the illustrated embodiment, the firing beam 326 comprises a first lockout notch 322 and a second lockout notch 324. The first lockout notch 322 has a first height relative to a lower edge 320 of the firing beam 326 and the second lockout notch 324 has a second height relative to the lower edge 320 of the firing beam 326. In certain embodiments, the second height is greater than the first height. The first lockout notch can be spaced from the second lockout notch by a tab 328 reinforcing the first lockout notch. Other aspects of a firing member 340 and firing beam 326 are substantially as described above with respect to the firing member and firing beam for use with the two-position lockout lever.

With reference to FIG. 21, in certain embodiments, a partially exploded view of a first jaw 372 and a second jaw 374 of a jaw assembly 370 is illustrated, with various components hidden for illustration of the empty jaw assembly lockout mechanism and the fired reload lockout mechanism. In certain embodiments, the lockout mechanisms comprise a first, empty jaw assembly lockout lever 380, a second, fired reload lockout lever 480, a biasing spring 390, a first lockout notch 322, and a second lockout notch 324. In the illustrated embodiment, the first lockout lever 380 and the second lockout lever 480 are each pivotably coupled to the second jaw 374 of the jaw assembly, and the first lockout lever 380 and the second lockout lever 480 are independently pivotable. In the illustrated embodiment, the first lockout lever 380 and the second lockout lever 480 are positioned on opposite sides of the firing member 340 and firing beam 326 and each pivot about a pivot axis that is transverse to a longitudinal axis of the jaw assembly 370. In certain embodiments, the first lockout lever 380 and the second lockout lever 480 pivot about the same pivot axis. In other embodiments, the pivot axis of the first lockout lever 380 can be longitudinally offset from the pivot axis of the second lockout lever 480.

With continued reference to FIG. 21, in the illustrated embodiment, the first lockout lever 380 has a proximal end 386, a distal end 382, and a pivot 384 positioned between the proximal end 386 and the distal end 382. The biasing spring 390 has a lower spring arm 392 that is positioned on an upper surface of the distal end 382 of the first lockout lever 380. The biasing spring 390 biases the distal end 382 of the first lockout lever 380 downwardly, towards the reload support of the second jaw 374. The biasing spring can further comprise at least one upper spring arm 394 that biases the first jaw 372 pivotally away from the second jaw 374 to position the jaw assembly in an open configuration. Thus the biasing spring 390 exerts a spring force on the distal end 382 of the first lockout lever 380 that tends to pivot the proximal end 386 of the first lockout lever 380 upwards, away from the reload support. As illustrated, with the firing member 340 and firing beam 326 in a fully retracted position, corresponding to an open jaw assembly, a proximally extending tail 347 on the firing member 340 engages the proximal end 386 of the first lockout lever 380, overcoming the force exerted by the biasing spring 390 and positioning the distal end 382 of the first lockout lever 380 in a raised position with respect to the reload support such that a reload cartridge can be inserted to the reload support.

With further reference to FIG. 21, the second lockout lever 480 has a proximal end 486, a distal end 482, and a pivot 484 positioned between the proximal end 486 and the distal end 482. In certain embodiments, a biasing member 490 is positioned on a lower surface of the distal end 482 of the second lockout lever 480. The biasing member 490 is configured to maintain the distal end 482 of the second locked lever 480 in a raised position when no reload cartridge is present in the jaw assembly. As illustrated, in certain embodiments, the biasing member 490 comprises a compressible puck positioned on the lower surface of the distal end 482 of the second lockout lever 480 to maintain the distal end 482 of the second lockout lever 480 in a raised position relative to the reload support. In other embodiments, other biasing members such as coil springs can be positioned on the lower surface of the distal end of the second lockout lever. In still other embodiments, the biasing member can be positioned on the reload support under the distal end of the second lockout lever.

Figure 22:
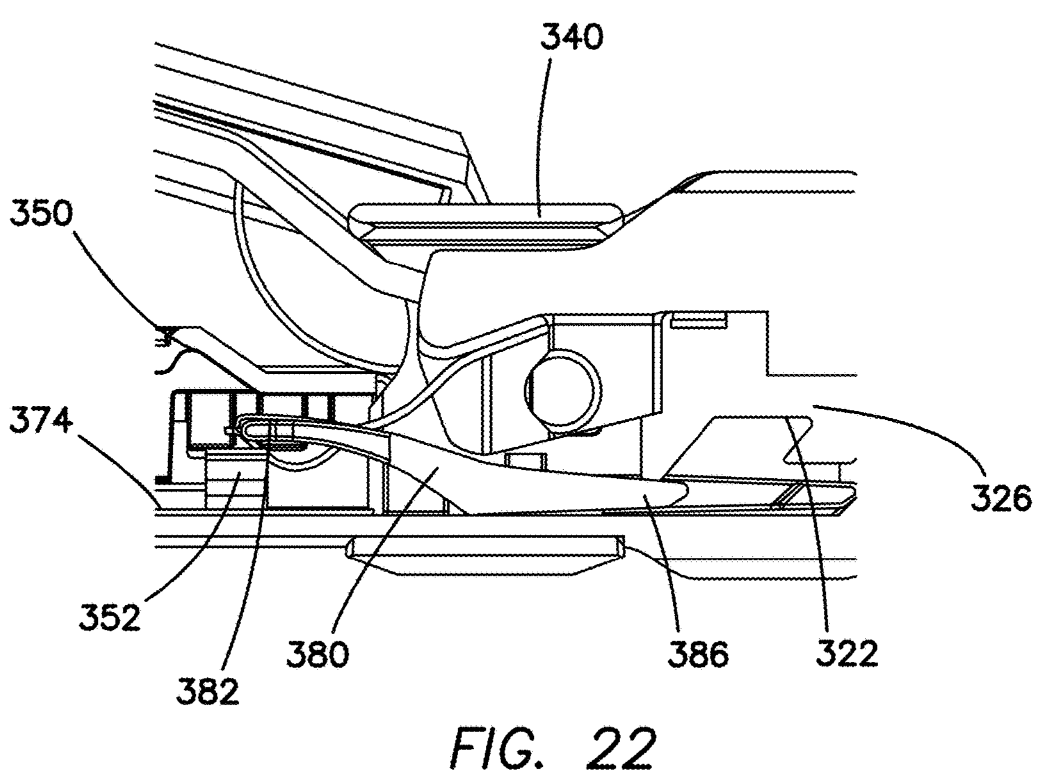
FIG. 22 is a cut away side view from a first side of a proximal end of the jaw assembly of FIG. 21 with an unfired reload cartridge inserted.
Figure 23:
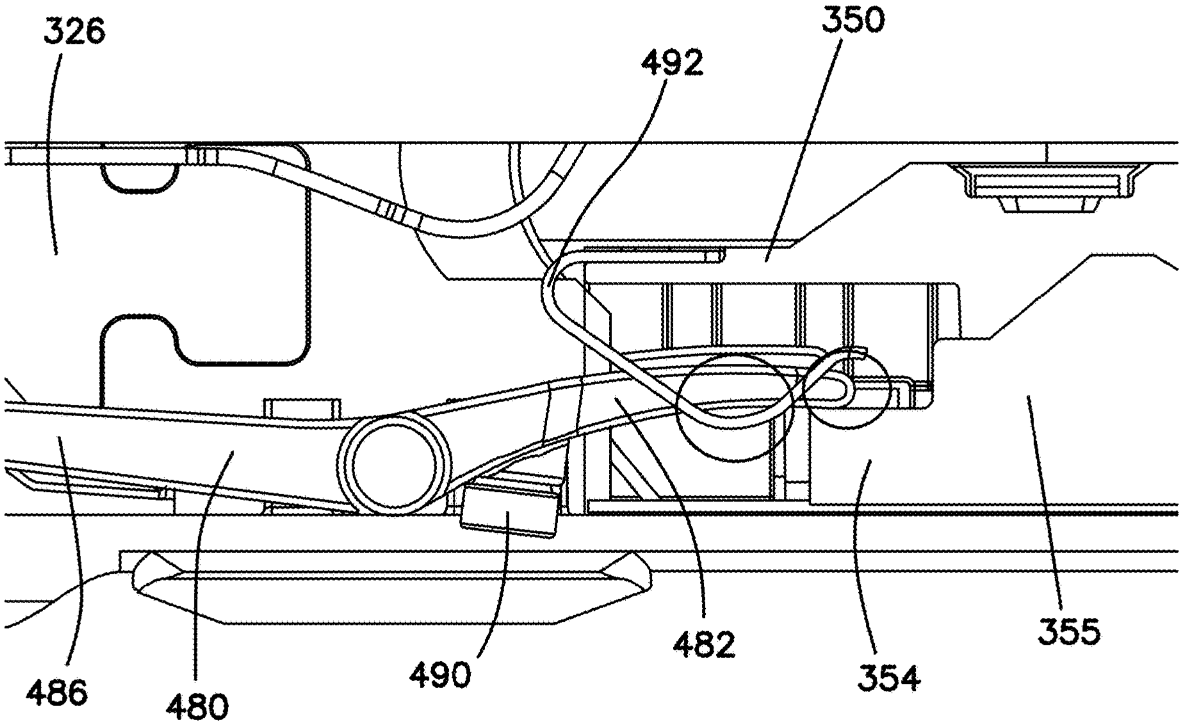
FIG. 23 is a cut away side view from a second side of a proximal end of the jaw assembly of FIG. 21 with an unfired reload cartridge inserted.

With reference to FIGS. 22 and 23, cut away views of the proximal end of the jaw assembly are illustrated with a reload 350 cartridge inserted and the firing member 340 and firing beam slightly longitudinally advanced towards a jaw assembly closed configuration. FIG. 22 illustrates a first side of the proximal end of the jaw assembly including the first lockout lever 380. FIG. 23 illustrates a second side of the proximal end of the jaw assembly including the second lockout lever 480. With an unfired reload 350 cartridge positioned in the jaw assembly, the empty jaw assembly lockout mechanism has been defeated and is in an unlocked configuration, and the fired reload lockout mechanism has been defeated and is in an unlocked configuration.

With reference to FIG. 22, as a reload cartridge 350 is inserted into the reload support of the second jaw 374 of the jaw assembly, a first lockout actuator 352 on a proximal end of the reload 350 is advanced proximally between the reload support and the distal end 382 of the first lockout lever 380. In the illustrated embodiment, the first lockout actuator 352 comprises a protruding surface on the reload cartridge. For example, in some embodiments, the reload cartridge can comprise a cartridge body partially surrounded by a metal jacket. The metal jacket can comprise a folded or raised surface that contacts a lower surface on the distal end 382 of the first lockout lever 380 to maintain a height of the distal end 382 of the first lockout lever 380 relative to the reload support when a reload 350 cartridge is present in the jaw assembly. With the distal end 382 of the first lockout lever 380 maintained at the height of the first lockout actuator 352, the proximal end 386 of the first lockout lever 380 is positioned at a height below a lower edge of the firing beam 326, away from the first lockout notch 322 and the second lockout notch. Accordingly, with a reload 350 cartridge in the reload support, the empty jaw assembly lockout mechanism has been defeated. In certain embodiments, the lockout mechanisms can be configured to allow translation of the firing beam 326 and firing member 340 with the empty jaw lockout mechanism defeated to allow some portion of the open close stroke of the jaw assembly with a reload cartridge present in the jaw assembly regardless of whether the reload has been fired.

With reference to FIG. 23, as a reload 350 cartridge is inserted, a proximally extending tail 354 on the slider 355 is positioned between the reload support and a lower surface of the distal end 482 of the second lockout lever 480. The biasing member 490 or compressible puck maintains the height of the distal end 482 of the second lockout lever 480 to receive the tail 354 of the slider 355 under the distal end 482 of the second lockout lever 480. In certain embodiments, the reload 350 cartridge further comprises a cartridge biasing spring 492 biasing an upper surface of the distal end 482 of the second lockout lever 480 downward towards the reload support.

With continued reference to FIG. 23, with the distal end 482 of the second lockout lever 480 at the height of the tail 354 of the slider 355, the proximal end 486 of the second lockout lever 480 is positioned at a height below a lower edge of the firing beam 326, away from the first lockout notch and the second lockout notch. Accordingly, with a reload 350 cartridge in the reload support, the fired reload lockout mechanism has been defeated. Thus, when an unfired reload 350 has been positioned in the reload support of the jaw assembly, both the empty jaw assembly lockout mechanism and the fired reload lockout mechanism have been defeated and a user can operate an operatively coupled handle assembly to advance the firing beam and firing member in a firing stroke to deploy staples from the reload 350 cartridge.

Figure 24:
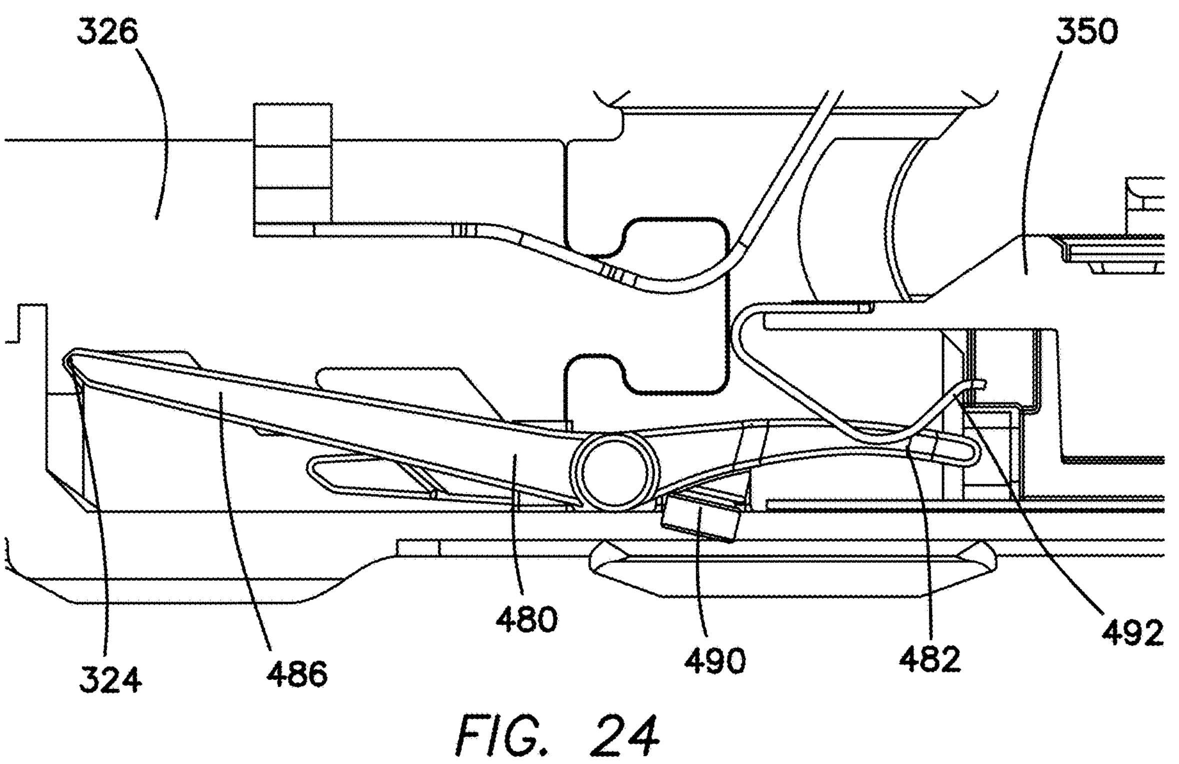
FIG. 24 is a cut away side view from a second side of a proximal end of the jaw assembly of FIG. 21 with a fired reload cartridge inserted.

With reference to FIGS. 24, a cut away view of the proximal end of the jaw assembly is illustrated with a partially or fully fired reload cartridge inserted and the firing member and firing beam slightly longitudinally advanced corresponding to a jaw assembly closed configuration. With a partially or fully fired cartridge positioned in the jaw assembly, the empty jaw assembly lockout mechanism has been defeated and is in an unlocked configuration, and the fired reload lockout mechanism is in a locked configuration.

With a fired reload cartridge inserted, the position of the first lockout lever on the first side of the jaw assembly is the same as described above with respect to an unfired reload cartridge (FIG. 22). Thus, once a reload cartridge has been at least partially fired, or if a previously-used reload cartridge has been reinserted into the reload support of the jaw assembly, the empty jaw assembly lockout mechanism is defeated.

With reference to FIG. 24, with a fired reload 350 cartridge inserted, a cartridge biasing spring exerts force on the distal end 482 of the second lockout lever 480 in a downward direction towards the reload support. The cartridge biasing spring 492 is configured to exert force sufficient to overcome the bias of the biasing member 490 between the reload support and the second lockout lever 480. In certain embodiments, the cartridge biasing spring 492 is coupled to the reload cartridge 350 at the proximal end thereof. In the illustrated embodiment, with no slider tail positioned in a proximal position, the cartridge biasing spring 492 exerts force sufficient to compress the compressible puck on the lower surface of the distal end 482 of the second lockout lever 480 such that the distal end 482 of the second lockout lever 480 is pivoted to a relatively low height relative to the reload support. With the distal end 482 of the second lockout lever 480 at this relatively low height, the proximal end 486 of the second lockout lever 480 is positioned at a height corresponding to the second lockout notch 324 of the firing beam 326 such that the fired reload lockout mechanism is in a locked configuration. As illustrated, once the firing beam is advanced by a user attempting to actuate the jaw assembly in an open-close stroke, the fired reload lockout mechanism engages as the proximal end 486 of the second lockout lever 480 seats within the second lockout notch 324 on the firing beam 326 to arrest further longitudinally distal motion of the firing beam 326.

With continued reference to FIG. 24, in the illustrated embodiment, the fired reload lockout mechanism is configured to allow a range of operation of the jaw assembly in the open-close stroke responsive to user input at the handle assembly. For example the position of the proximal end of the second lockout lever and second lockout notch can be selected to provide engagement of the fired reload lockout mechanism at a position of the firing beam corresponding to a closed or almost closed configuration of the jaw assembly. Thus, advantageously after firing staples from a reload cartridge, a user can grasp tissue with the jaw assembly to assess tissue thickness and consistency without removing the stapling device from the surgical site. Moreover, the fired reload lockout mechanism can be configured to prevent a user from selecting a firing operation at a handle assembly of the stapling device by engaging before completion of the open-close stroke of the jaw assembly. Thus, a user can be prevented from inadvertently advancing the firing member and firing beam into a position corresponding to the firing stroke of the jaw assembly, in which a cutting blade of the firing beam may be accessible to tissue.

Figure 25:
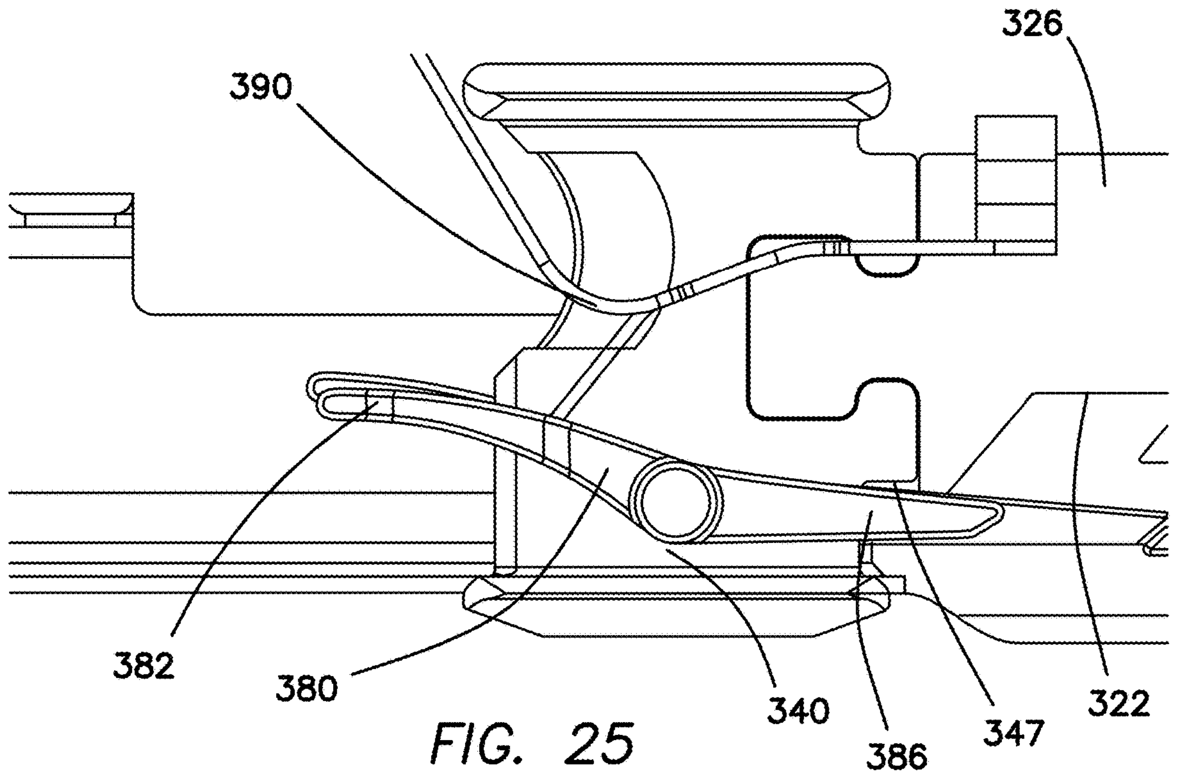
FIG. 25 is a cut away side view from a first side of a proximal end of the jaw assembly of FIG. 21 with no reload cartridge inserted.
Figure 26:
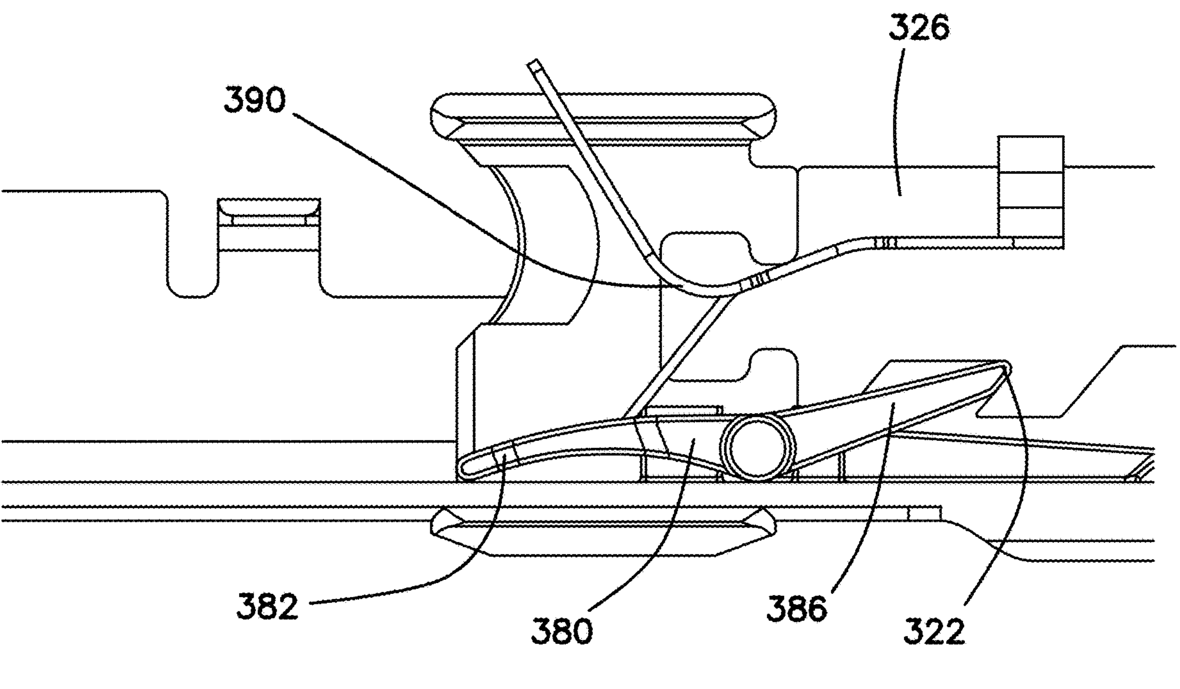
FIG. 26 is a cut away side view from a first side of a proximal end of the jaw assembly of FIG. 21 with no reload cartridge inserted and the firing beam longitudinally advanced.
Figure 27:
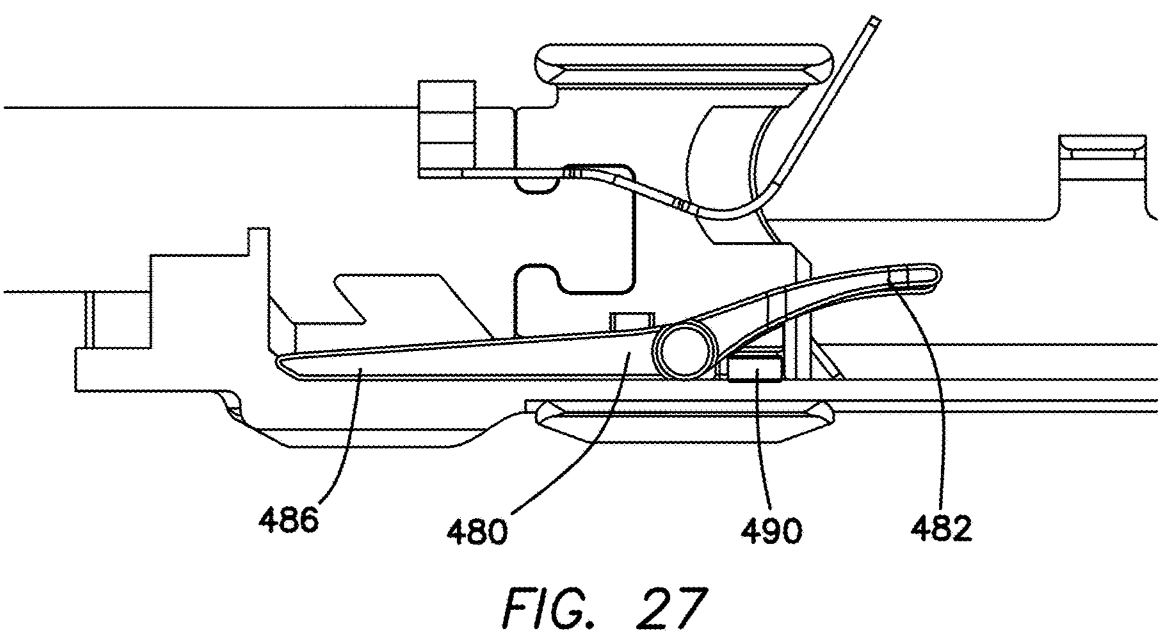
FIG. 27 is a cut away side view from a second side of a proximal end of the jaw assembly of FIG. 21 with no reload cartridge inserted.

With reference to FIGS. 25, 26 and 27, cut away views of the proximal end of the jaw assembly are illustrated with no reload cartridge inserted and the firing member and firing beam longitudinally fully retracted (FIGS. 25, 27) or substantially fully retracted (FIG. 26), corresponding to a jaw assembly open configuration. FIG. 25 illustrates a first side of the proximal end of the jaw assembly including the first lockout lever 380. FIG. 26 illustrates the first side of the proximal end of the jaw assembly with the firing member slightly advanced illustrating operation of the empty jaw assembly lockout mechanism. FIG. 27 illustrates a second side of the proximal end of the jaw assembly including the second lockout lever 480. In the illustrated embodiment, with no reload cartridge positioned in the jaw assembly, the empty jaw assembly lockout mechanism is in a locked configuration, and the fired reload lockout mechanism is in an unlocked configuration.

With reference to FIG. 25, with no reload cartridge inserted and the jaw assembly in the open configuration, the position of the first lockout lever 380 is initially maintained with the distal end 382 of the first lockout lever 380 raised from the reload support to receive a reload cartridge. With the jaw assembly in the open configuration, the firing beam 326 is in a fully retracted position, and a tail 347 on the firing member 340 rests on the proximal end 386 of the first lockout lever 380 to position the distal end 382 of the first lockout lever 380 to receive the reload cartridge. However, if a user attempts to actuate the jaw assembly in an open-close stroke (FIG. 26), the tail 347 on the firing member 340 will be longitudinally advanced off of the proximal end 386 of the first lockout lever 380. The biasing spring 390 can exert a force on an upper surface of the distal end 382 of the first lockout lever 380 to pivot the first lockout lever 380 such that the proximal end 386 of the first lockout member is positioned at a height from the reload support corresponding to a height of the first lockout notch 322 on the firing beam 326. With reference to FIG. 26, if a user continues to attempt to actuate the jaw assembly in an open-close stroke, the proximal end 386 of the first lockout lever 380 will seat in the first lockout notch 322 on the firing beam 326 upon initial distal movement of the firing beam. Thus, the empty jaw assembly lockout mechanism is in a locked configuration.

With continued reference to FIGS. 25-26, the empty jaw assembly lockout mechanism can be configured to restrict further distal movement of the firing beam during an initial portion of the open-close stroke of the jaw assembly. For example, the size of the tail 347 on the firing member 340, the position of the proximal end 386 of the first lockout lever 380 and the first lockout notch 322 can be configured to arrest the firing beam 326 upon initial distal movement of the firing beam 326. Accordingly, the empty jaw assembly lockout mechanism would engage with the jaw assembly in a partially or substantially open configuration. Desirably, this engagement of the empty jaw assembly lockout mechanism would indicate to a user that the jaw assembly was empty before the jaw assembly would be introduced to a surgical site.

With reference to FIG. 27, with no reload cartridge inserted in the jaw assembly, the biasing member 490 or compressible puck maintains the distal end 482 of the second lockout lever 480 in a raised position relative to the reload support. With the distal end 482 of the second lockout lever 480 at this raised height, the proximal end 486 of the second lockout lever 480 is positioned adjacent the reload support such that the proximal end 486 of the second reload lever 480 is at a relatively low height adjacent to the reload support and spaced away from the first lockout notch and the second lockout notch of the firing beam 326. Thus, the fired reload lockout mechanism is in an unlocked configuration. As illustrated, once the firing beam is advanced by a user attempting to actuate the jaw assembly in an open-close stroke, the fired reload lockout mechanism remains in the unlocked configuration, and the proximal end of the second lockout lever remains adjacent the reload support.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims.

What is claimed is:

1. A surgical stapler comprising:
- an elongate shaft having a proximal end, a distal end, and a longitudinal axis extending between the proximal end and the distal end;
- a firing beam having a proximal end, distal end, and a lower edge, at least a portion of the firing beam being longitudinally slidable within the elongate shaft, the firing beam comprising:
  - a first lockout notch having a first height from the lower edge; and
  - a second lockout notch having a second height from the lower edge, the second height different from the first height; and
- a jaw assembly at the distal end of the elongate shaft, the jaw assembly comprising:
  - a first jaw defining an anvil;
  - a second jaw; and
  - a lockout mechanism engageable with the first lockout notch with the jaw assembly in a first operational configuration, engageable with the second lockout notch with the jaw assembly in a second operational configuration, and spaced from the first lockout notch and the second lockout notch with the jaw assembly in a third operational configuration.

2. The surgical stapler of claim 1, wherein the second jaw comprises a reload support and further comprising a reload cartridge removably positionable in the reload support.

3. The surgical stapler of claim 2, wherein the first operational configuration comprises an empty jaw assembly such that the lockout mechanism engages the first lockout notch upon distal longitudinal sliding of the firing beam when the reload cartridge is removed from the reload support.

4. The surgical stapler of claim 2, wherein the second operational configuration comprises a fired reload cartridge such that the lockout mechanism engages the second lockout notch upon distal longitudinal sliding of the firing beam when a fired reload cartridge is positioned in the reload support.

5. The surgical stapler of claim 2, wherein the third operational configuration comprises an unfired reload cartridge such that the lockout mechanism is spaced from the first lockout notch and the second lockout notch upon distal longitudinal sliding of the firing beam when an unfired reload cartridge is positioned in the reload support.

6. The surgical stapler of claim 1, wherein the first lockout notch and the second lockout notch are contiguous.

7. The surgical stapler of claim 6, wherein the lower edge is relieved over a longitudinal span corresponding to the first lockout notch and the second lockout notch.

8. The surgical stapler of claim 1, wherein the lockout mechanism comprises a lockout lever pivotably coupled to the second jaw.

9. The surgical stapler of claim 8, wherein the lockout lever comprises a proximal end, a distal end opposite the proximal end, and a pivot coupled to the second jaw between the proximal end and the distal end.

10. The surgical stapler of claim 9, wherein the proximal end of the lockout lever is movable between a first lockout height corresponding to the first height of the first notch, a second lockout height corresponding to the second height of the second notch, and an unlocked height.

11. The surgical stapler of claim 10, wherein the second jaw comprises a reload support and further comprising a reload cartridge removably positionable in the reload support.

12. The surgical stapler of claim 11, wherein the reload cartridge comprises a first lockout actuator engageable with the distal end of the lockout lever and a second lockout actuator engageable with the distal end of the lockout lever.

13. The surgical stapler of claim 12, wherein the first lockout actuator is longitudinally fixed with respect to the reload cartridge.

14. The surgical stapler of claim 12, wherein the second lockout actuator is longitudinally slidable with respect to the reload cartridge.

15. The surgical stapler of claim 1, wherein the lockout mechanism comprises a first lockout lever pivotably coupled to the second jaw and a second lockout lever pivotably coupled to the second jaw and pivotable independently from the first lockout lever.

16. The surgical stapler of claim 15, wherein the first lockout lever is engageable with the first lockout notch.

17. The surgical stapler of claim 15, wherein the second lockout lever is engageable with the second lockout notch.

18. The surgical stapler of claim 15, wherein the first lockout notch is longitudinally spaced from the second lockout notch on the firing beam.

19. A surgical stapler comprising:

an elongate shaft having a proximal end, a distal end, and a longitudinal axis extending between the proximal end and the distal end;

a firing beam having a proximal end and a distal end, at least a portion of the firing beam being longitudinally slidable within the elongate shaft;

a jaw assembly at the distal end of the elongate shaft, the jaw assembly comprising:

a first jaw defining an anvil;

a second jaw defining a reload support configured to receive a reload cartridge; and a lockout mechanism engageable with the firing beam; and a reload cartridge having a plurality of staples deployable therefrom, the reload cartridge removably positionable in the reload support, and the reload cartridge comprising:

a cartridge body;

a first lockout actuator positioned on the cartridge body and stationary with respect to the cartridge body to engage the lockout mechanism when the reload cartridge is positioned in the reload support; and a second lockout actuator positioned within the cartridge body and longitudinally slidable with respect to the cartridge body to engage the lockout mechanism when the reload cartridge is positioned in the reload support and the plurality of staples remain undeployed.

20. The surgical stapler of claim 19, wherein the first lockout actuator comprises a ramped boss positioned on the cartridge body, and wherein the reload cartridge comprises a slider longitudinally distally movable within the cartridge body to deploy the plurality of staples from the reload cartridge, the slider comprising a slider tail, and wherein the second lockout actuator comprises the slider tail.

* * * * *